(12) United States Patent
Jung et al.

(10) Patent No.: US 8,124,358 B2
(45) Date of Patent: Feb. 28, 2012

(54) METHODS OF SCREENING FOR COMPOUNDS THAT INHIBIT BINDING BETWEEN AMYLOID-β(Aβ) AND FC-γ RECEPTOR IIB (FCγRIIB)

(75) Inventors: Yong-Keun Jung, Seoul (KR); Sungmin Song, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 445 days.

(21) Appl. No.: 11/947,612

(22) Filed: Nov. 29, 2007

(65) Prior Publication Data

US 2009/0123459 A1  May 14, 2009

(30) Foreign Application Priority Data

Nov. 9, 2007 (KR) .......................... 10-2007-114468

(51) Int. Cl.
G01N 33/567 (2006.01)
G01N 33/566 (2006.01)
G01N 33/58 (2006.01)
G01N 33/60 (2006.01)

(52) U.S. Cl. .......................... 435/7.21; 435/7.1; 435/7.8

(58) Field of Classification Search .................. None
See application file for complete search history.

(56) References Cited

U.S. PATENT DOCUMENTS

| 2002/0061515 A1* | 5/2002 | Lynch et al. ..................... 435/4 |
| 2004/0185045 A1* | 9/2004 | Koenig et al. ............... 424/144.1 |
| 2004/0248766 A1* | 12/2004 | LeBlanc ........................... 514/2 |
| 2008/0014141 A1* | 1/2008 | Huber et al. .................... 424/9.1 |

OTHER PUBLICATIONS

Gylys KH et al. Apolipoprotein E enhances uptake of soluble but not aggregated amyloid-beta protein into synaptic terminals. J Neurochem. 2003; 84:1442-1451.*

Saavedra L et al. Internalization of beta-amyloid peptide by primary neurons in the absence of Apolipoprotein E. J Biol Chem. Dec. 2007; 282(49):35722-35732; Epub Oct. 2, 2007.*

Nakamura, et al., "A role of FcγRIIB in the development of collagen-induced arthritis," *Biomedicine & Pharmacotherapy*, 58:292-298 (2004).

Arancio, et al., "RAGE potentiates Aβ induced perturbation of neuronal function in transgenic mice," *The EMBO Journal*, 23:4096-4105 (2004).

Lustbader, et al. "ABAD Directly Links Aβ to Mitochondrial Toxicity in Alzheimer's Disease," *Science*, 304:448-452 (2004).

Takuma, et al. "ABAD enhances Aβ-induced cell stress via mitochondrial dysfunction," *The FASEB Journal*, 19:597-598 (2005) Epub (2005).

* cited by examiner

*Primary Examiner* — Elizabeth C Kemmerer
*Assistant Examiner* — Kimberly A Ballard
(74) *Attorney, Agent, or Firm* — Klarquist Sparkman, LLP

(57) ABSTRACT

Disclosed herein are methods of diagnosing, preventing and treating Alzheimer's disease based on the use of an inhibitor for the binding of amyloid-β (Aβ) to FcγRIIb, and a method of screening the inhibitor. The inhibitor is selected from the group consisting of an FcγRIIb protein or a variant thereof, an FcγRIIb extracellular domain, an anti-FcγRIIb antibody, an FcγRIIb-specific peptide and an FcγRIIb-specific siRNA. The inhibitor reduces the toxic signaling and intracellular translocation of Aβ and the neurotoxicity, neuronal cell death and memory impairment mediated by Aβ by inhibiting the binding between Aβ and FcγRIIb. Thus, the inhibitor is useful in the diagnosis, prevention and treatment of Alzheimer's disease.

7 Claims, 13 Drawing Sheets

Fig. 1
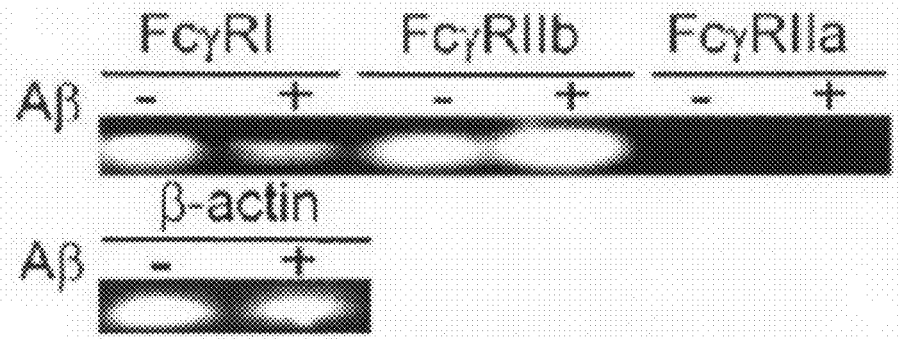
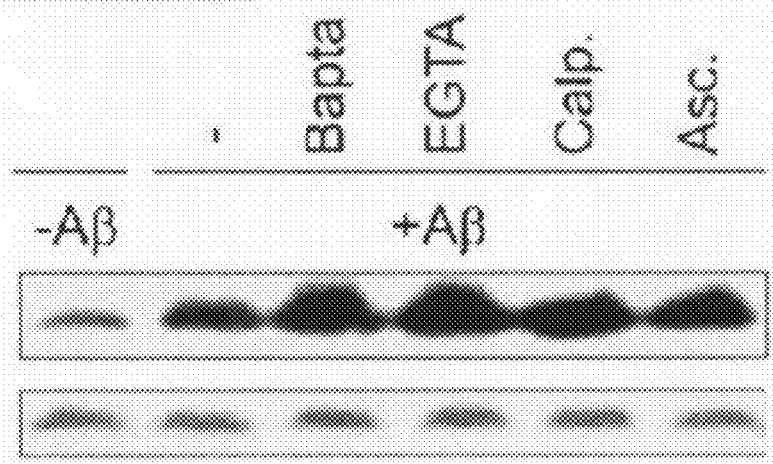
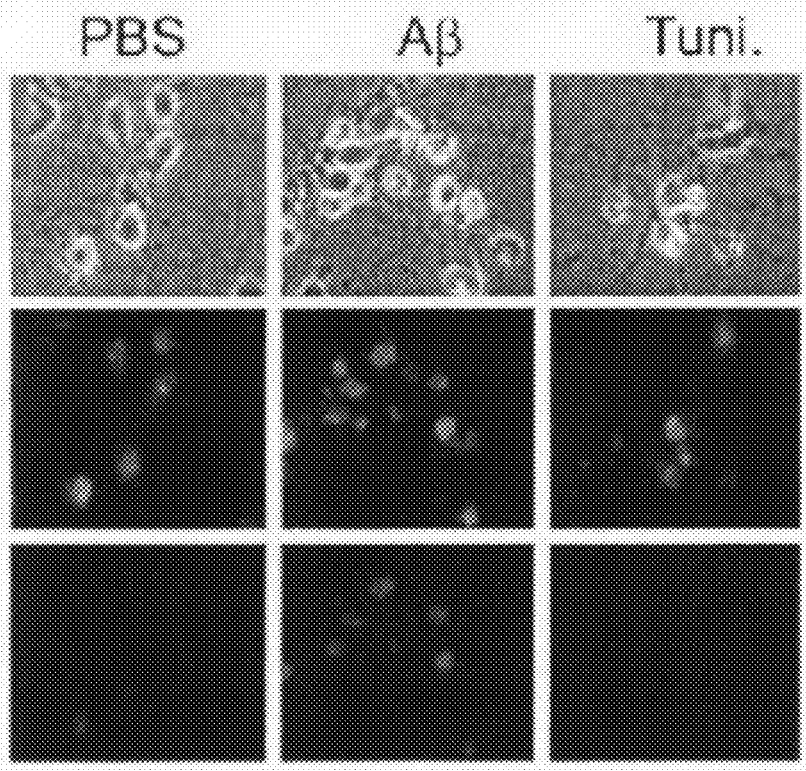

Fig. 3
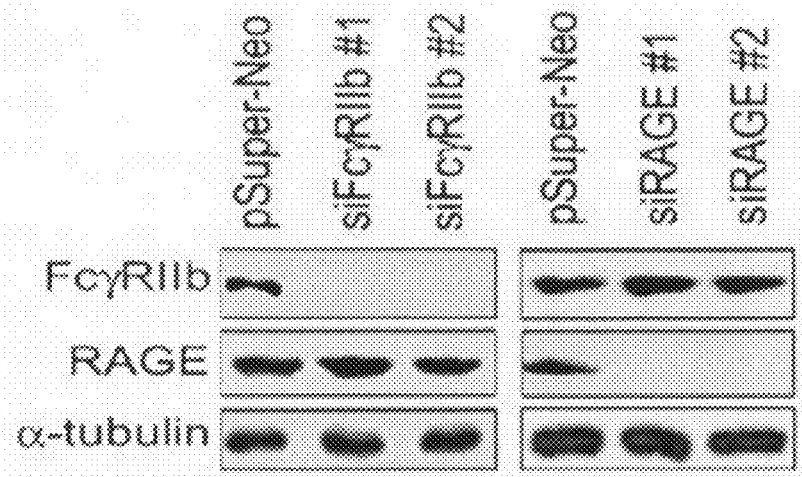
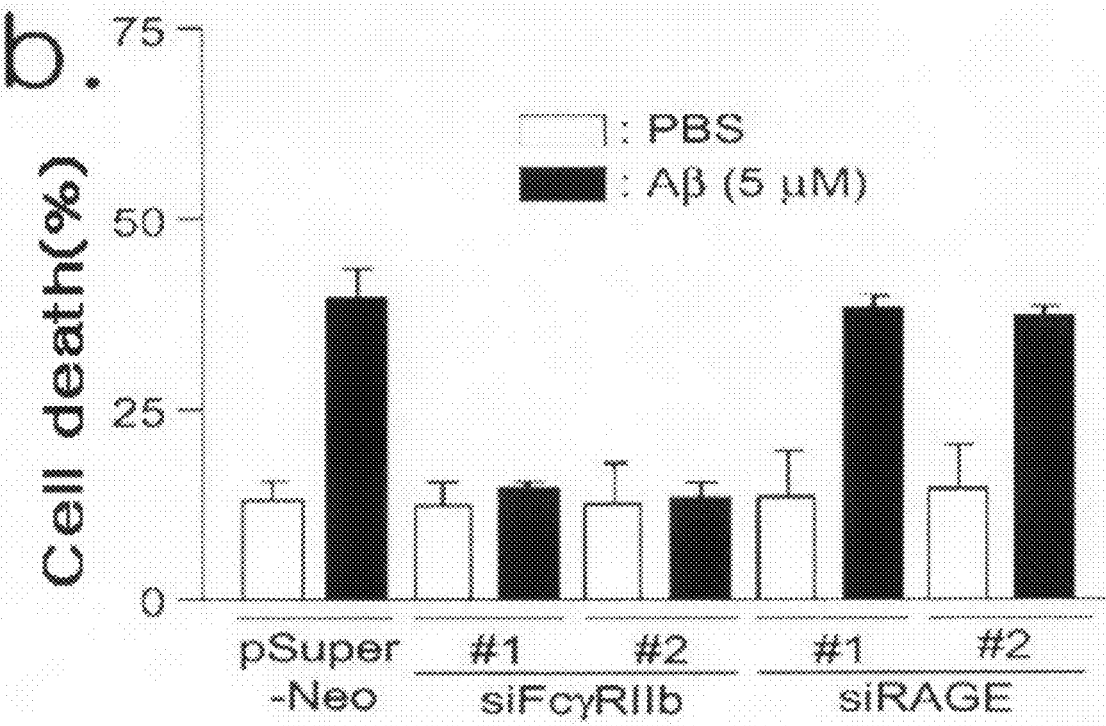

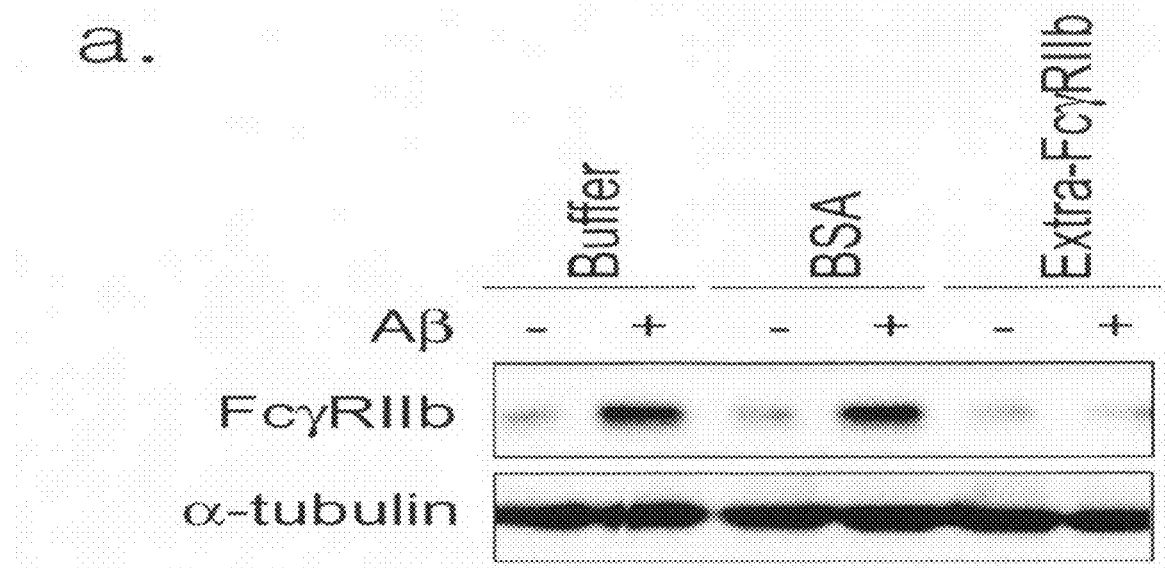
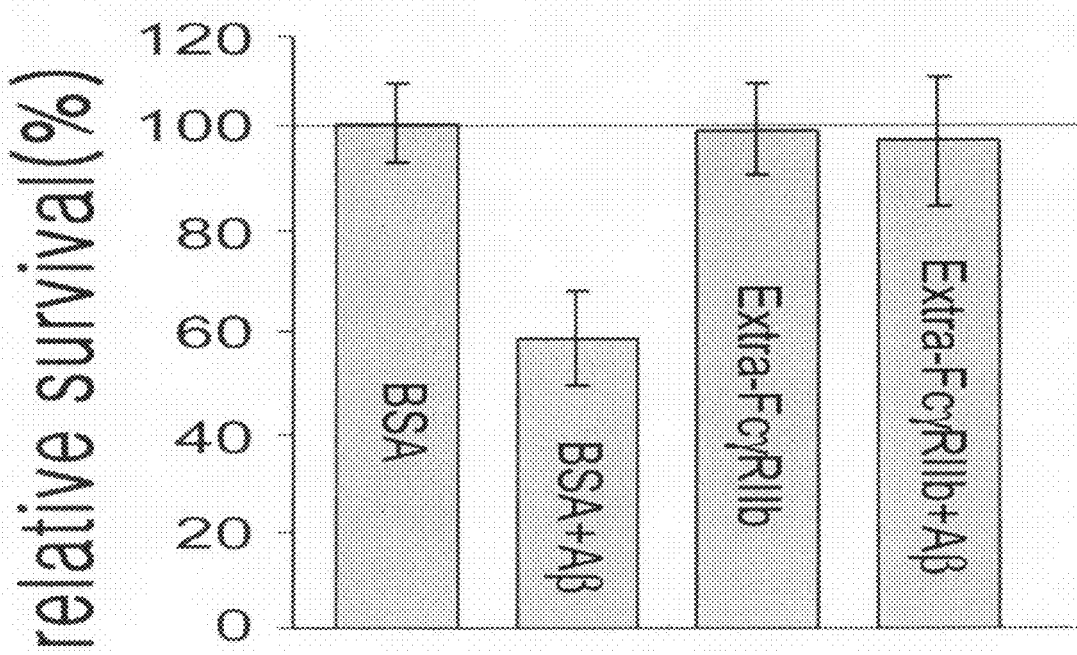
Fig. 4

Fig. 8
a.
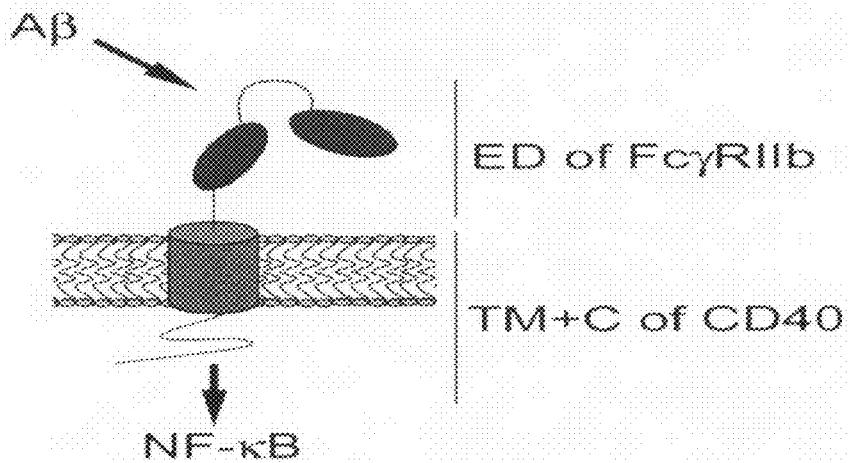
b.
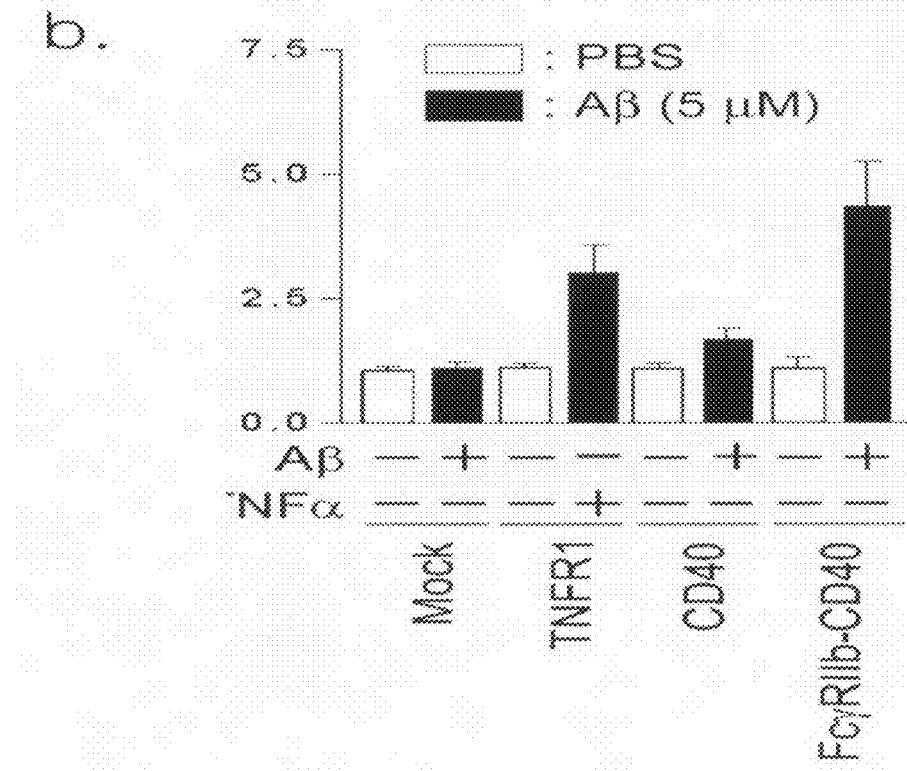

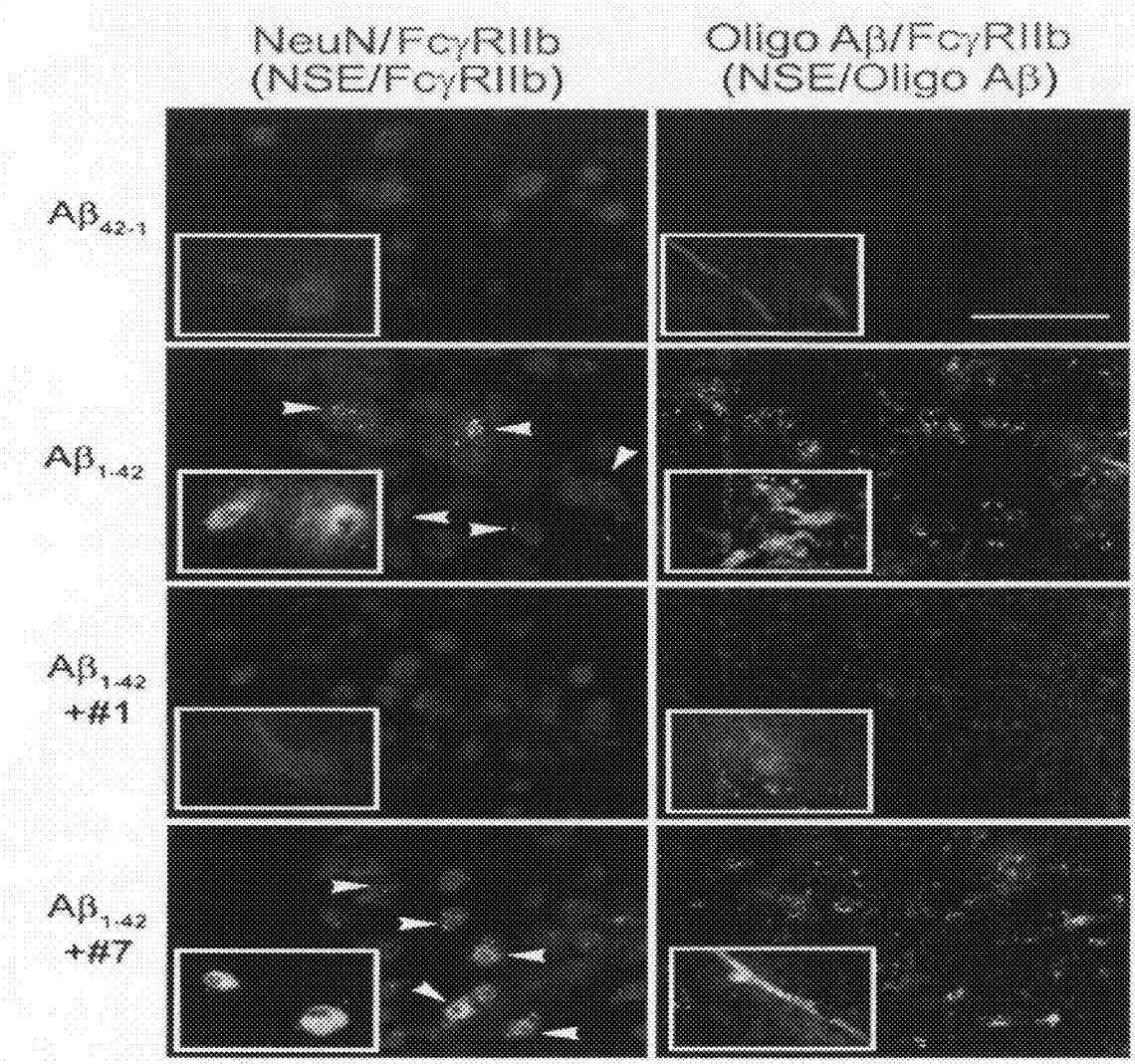

METHODS OF SCREENING FOR COMPOUNDS THAT INHIBIT BINDING BETWEEN AMYLOID-β(Aβ) AND FC-γ RECEPTOR IIB (FCγRIIB)

BACKGROUND OF THE INVENTION

1. Field of the Invention

The present invention relates to methods of diagnosing, preventing and treating Alzheimer's disease based on the use of an inhibitor for the binding of amyloid-β to FcγRIIb, and a method of screening the inhibitor. More particularly, the present invention relates to methods of diagnosing, preventing and treating Alzheimer's disease using an inhibitor of the binding between amyloid-β and FcγRIIb, which is selected from the group consisting of an FcγRIIb protein or a variant thereof, an FcγRIIb extracellular domain, an anti-FcγRIIb antibody, a specific peptide and an FcγRIIb-specific siRNA, and a method of screening the inhibitor.

2. Description of the Related Art

About 50-70% of all people having dementia suffer from Alzheimer's disease (hereinafter, referred to simply as "AD"), which is caused by the progressive degeneration of nerve cells in the brain, resulting in the loss of cognitive ability. AD is divided into two forms: familial AD, which has genetic links and runs in families, and sporadic AD, which develops in many people for no obvious reason. AD patients typically have multiple cognitive deficiencies, which are manifested by memory impairment and psychological symptoms such as psychosomatic abnormalities, including increased anxiety and hypersensitivity.

Two pathological hallmarks are seen in the brains of patients who die of AD: senile plaques and neurofibrillary tangles. Senile plaques are extracellular accumulations of proteins and dead cells, and are primarily composed of amyloid-β (Aβ) peptides (Hardy, J. et al., *Nat Neurosci.* 1:355-358, 1998). The progressive loss of cognitive ability, which is the major pathological feature of AD patients, seems to be caused by the aberrant deposition of Aβ.

Aβ is produced from amyloid precursor protein (APP) through proteolytic cleavage. APP is cleaved by β-secretase (BACE) and γ-secretase, yielding Aβ (Craven, R., *Nat Rev. Neurosci.* 2: 533, 2001; David, H. S. et al., *Nat Rev. Neurosci.* 2: 595-598, 2001; Yankner, B. A., *Neuron* 16: 921-932, 1996; Selkoe, D. J., *Nature* 399: A23-A31, 1999).

Studies associated with AD to date resulted in the development of preventive and therapeutic agents for AD mainly using agents inhibiting Aβ production, such as secretase inhibitors, or inhibitors of neurotoxicity, such as antioxidants. Current medications for AD include nicotinic receptor agonists, such as ABT-418; muscarinic receptor agonists, such as Xanomeline and YM-976; acetylcholine precursors, such as lecithin and acetyl-L-carnitine; metal chelators, such as desferrioxamine and clioquinol; beta-sheet breakers, such as iAβ5 and iAβ11; antioxidants, such as vitamin E, *Ginkgo biloba*, melatonin and idebenone; sAPP releasing agents, such as nicotine, acetylcholine and carbachol; β-secretase or γ-secretase inhibitors, such as OM99-1, OM99-2, OM99-3 and Z-VLL-CHO; non-steroidal anti-inflammatory drugs (NSAIDs), such as ibuprofen and indomethacin; hormones such as estrogen; vaccines, such as AN-1792; and cholesterol-lowering agents, such as simvastatin and atorvastatin. However, most medications are only marginally helpful in slightly relieving the pathological symptoms of AD or slowing AD progression, or are difficult to apply in practice due to their toxicity. Thus, there remains an urgent need for the development of stable and effective drugs for AD treatment.

Recent AD-associated studies have been focused on the identification of neurotoxic mechanisms of Aβ. Pro-apoptotic genes, such as prostate apoptosis response-4 (Par-4), tau protein kinase 1 (GSK-3β), Calsenilin/DREAM/KChIP3, and cell death-promoting gene 5 (DP5), are shown to be overexpressed or their activities are increased in neuronal cells cultured in the presence of Aβ or neuronal cells from AD patients. The blocking of the functions of the proteins reduces Aβ-induced neuronal death (Guo, Q. et al., *Nat. Med.* 4:597-562, 1998; Takashima, A. et al., *Proc. Natl. Acad. Sci. USA* 90:7789-7793, 1993; Jo, D. G. et al., *FASEB J.* 15:589-591, 2001; Imaizumi, K. et al., *J. Biol. Chem.* 274:7975-7981, 1999). However, these reports are not sufficient to identify an intracellular signaling pathway for Aβ-induced neuronal toxicity so as to develop AD drugs for preventing Aβ-induced neuronal loss. To date, inhibitors of Aβ-induced neurotoxicity have not been found even in vitro.

An important step to define neurotoxic mechanisms of Aβ is to find a receptor for Aβ on neuronal cells. Many efforts have been made, but no specific receptor for Aβ has been identified yet. Several proteins interacting with Aβ, including receptors for advanced glycation end-product (RAGE) (Arancio, O. et al., *EMBO J.* 23:4096-4105, 2004) and amyloid-beta binding alcohol dehydrogenase (ABAD) (Takuma, K. et al., *FASEB J.* 19:597-598, 2005), were reported to be receptors for Aβ. However, such proteins have been shown to serve as cellular cofactors, rather than functioning to fundamentally modulate signal transduction in neuronal cells or neuronal toxicity. Thus, they are not likely to be receptors for Aβ. This is because they were identified not using a knock-out method but through the observation that their overexpression increases signal transduction and neuronal toxicity.

On the other hand, Fcγ receptor IIb (FcγRIIb), expressed on immune cells, has been known to be a receptor having low binding affinity to immunoglobulin G. Individuals having a mutation in the FcγRIIb gene (FcγRIIb[I232T]), leading to abnormal immune responses, are susceptible to autoimmune diseases. Also, the FcγRIIb receptor has recently been known to play a regulatory role in arthritis (Nakamura, A. et al., *Biomed. Pharmacother.* 58:292-298, 2004). However, the involvement of FcγRIIb in dementia and its potential as a therapeutic target for dementia have not been known.

The inventors of this application found for the first time that FcγRIIb serves as a receptor for Aβ as well as playing an immunoregulatory role. In particular, the present inventors found that FcγRIIb acts as a protein mediating Aβ neurotoxicity and serves as a receptor in an Aβ-initiated toxic signaling pathway, through which FcγRIIb binds Aβ as the first event of the toxic signaling in neuronal cells and transduces the cell death signal into the cells. The present inventors also found that FcγRIIb enhances Aβ deposition, associated with memory impairment in AD, within neuronal cells. Based on these findings, the present inventors further found that an FcγRIIb protein or a variant thereof, an FcγRIIb extracellular domain, an anti-FcγRIIb antibody, an FcγRIIb-specific peptide and an FcγRIIb-specific siRNA suppress neuronal cell death and prevent memory loss in subjects, thereby leading to the present invention.

SUMMARY OF THE INVENTION

It is therefore an object of the present invention to provide an inhibitor for the binding of Aβ to FcγRIIb.

It is another object of the present invention to provide a method of screening an inhibitor for the binding of Aβ to FcγRIIb.

It is a further object of the present invention to provide a diagnostic method and a diagnostic kit for Alzheimer's disease.

It is yet another object of the present invention to provide a method of preventing and treating Alzheimer's disease.

In order to accomplish the above objects, the present invention provides a method of preventing and treating Alzheimer's disease by inhibiting the binding of Aβ to FcγRIIb.

The present invention also provides an inhibitor for the binding of Aβ to FcγRIIb. The inhibitor includes an FcγRIIb protein or a variant thereof, an FcγRIIb extracellular domain, an anti-FcγRIIb antibody, an FcγRIIb-specific peptide, and an FcγRIIb-specific siRNA.

The present invention further provides a method of screening an agent inhibiting the interaction between Aβ and FcγRIIb. The screening method includes screening an agent inhibiting the activity of FcγRIIb, an agent suppressing the expression of FcγRIIb, an agent inhibiting the transduction of the toxic signal of Aβ into neuronal cells through FcγRIIb, and an agent inhibiting the interaction between Aβ and FcγRIIb.

The present invention still further provides a method of diagnosing Alzheimer's disease comprising determining the expression level of FcγRIIb.

The present invention still further provides a kit for diagnosing Alzheimer's disease comprising determining the expression level of FcγRIIb.

The present invention still further provides a method of preventing and treating Alzheimer's disease based on the use of the method of inhibiting the interaction between Aβ and FcγRIIb.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows the FcγRIIb expression, increased upon exposure to $A\beta_{1-42}$, which was detected using RT-PCR (a), Western blotting (b) and immunostaining (c) (Aβ: $A\beta_{1-42}$; Bapta: Bapta-AM; Calp.: Calpeptin; Asc.: Ascorbic acid; Tuni: tunicamycin);

FIG. 3 shows the inhibition of neuronal cell death using a siRNA against FcγRIIb and a siRNA against RAGE (b), wherein the expression of each protein was detected using Western blotting (a) (pSuper-Neo: void vector; siFcγRIIb #1: siRNA-expressing cell line #1; siFcγRIIb #2: siRNA-expressing cell line #2; siRAGE #1: siRNA-expressing cell line #1; siRAGE #2: siRNA-expressing cell line #2);

FIG. 4 shows the increased survival of Aβ-exposed cells when treated with an FcγRIIb extracellular domain (ED) (b), wherein the expression of each protein was detected using Western blotting (a) (Extra-FcγRIIb: FcγRIIb-ED);

FIG. 8 shows the schematic structure of an FcγRIIb-CD40 chimeric protein (a), and the stimulation of NF-κB activation when $A\beta_{1-42}$ binds FcγRIIb (b);

FIG. 13 shows the results of immunostaining for intraneuronal accumulation of $A\beta_{1-42}$ in neurons treated with peptides inhibiting the binding between $A\beta_{1-42}$ and FcγRIIb.

DESCRIPTION OF THE PREFERRED EMBODIMENTS

The terms used herein will have the following meanings.

The term "peptide" refers to a molecule in which two or more amino acids are linked via peptide bonds. The peptide can be synthesized through chemical synthesis, and also can be generated using typical genetic recombination technology.

The term "siRNA" refers to a RNA molecule that binds to a specific sequence in cells and thus knocks out a target gene. The siRNA can be prepared through the chemical synthesis of RNA oligonucleotides, small RNA synthesis using in vitro transcription, digestion of long dsRNA synthesized by in vitro transcription with RNase III or Dicer, expression from a siRNA expression plasmid or viral vector in cells, and expression from a PCR-derived siRNA expression cassette in cells.

The term "variant" refers to a peptide in which one or more amino acids, excluding amino acids critical in exerting its function, have been replaced, but which retains its innate function.

The term "interaction inhibitor" refers to a substance that inhibits interactions between proteins. The inhibitor is intended to indicate a composition including proteins, antibodies and peptides inhibiting the association between proteins, or an expression inhibitor.

The term "expression inhibitor" refers to a substance that suppresses the transcription or translation of a target gene, and is intended to indicate a composition including molecules commonly used for expression suppression, such as siRNAs or antisense nucleotides, which have a sequence complementary to a target gene.

The term "control group" refers to a test group that is treated with a buffer alone, used for dissolving a compound to be tested, or a test group that is treated with a compound known not to affect the function of a protein to be tested.

The term "FcγRIIb chimeric protein" refers to a chimeric (or fusion) protein of FcγRIIb with an effector protein (a protein activating the expression, color development or color change of a specific protein or cellular signal transduction upon the interaction between FcγRIIb and Aβ).

Hereinafter, the present invention will be described in detail.

I. The Present Invention Provides a Method of Preventing and Treating AD by Inhibiting the Binding of Aβ to FcγRIIb.

Figure 2:
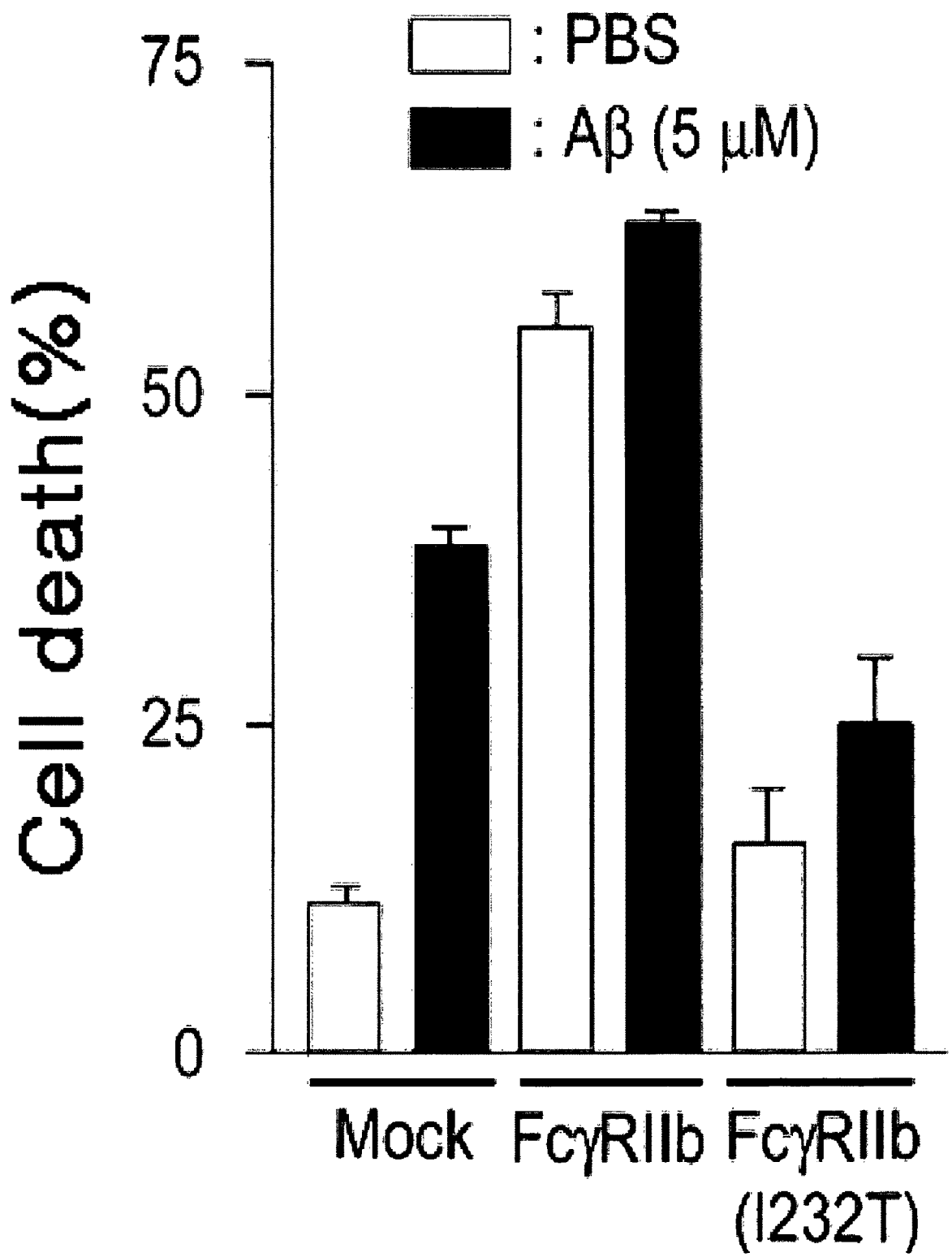
FIG. 2 shows neuronal cell death induced by overexpression of FcγRIIb and an FcγRIIb mutant.

The inventors of this application identified a receptor for Aβ, which is the major pathological cause of AD, on neuronal cells, and, based on this finding, developed a method of preventing and treating AD by inhibiting the association between Aβ and FcγRIIb. The expression of FcγRIIb was found to increase in neuronal cells exposed to Aβ (FIG. 1). Then, a FcγRIIb wild type and a FcγRIIb variant were prepared and administered to neuronal cells along with Aβ. As a result, cells treated with the FcγRIIb variant were found to exhibit reduced cell death rates (FIG. 2). These results indicate that FcγRIIb mediates Aβ signaling.

The present inventors prepared siRNAs to suppress the transcription of FcγRIIb and RAGE, which is known to be a cell surface receptor for Aβ (panel a, FIG. 3). The transcriptional suppression of RAGE expression did not result in any increase in cell survival, whereas all cells survived when the transcription of FcγRIIb was suppressed (panel b, FIG. 3). These results indicate that FcγRIIb rather than RAGE is the direct cell surface protein for Aβ signaling.

Then, an FcγRIIb extracellular domain was prepared, and neuronal cells exposed to Aβ were treated with this extracellular domain and examined for cell survival rates. The increased expression of FcγRIIb due to exposure to Aβ was suppressed (panel a, FIG. 4), and the relative cell viability was increased to that of cells not exposed to Aβ (panel b, FIG. 4). These results indicated that the FcγRIIb-mediated neuronal transduction of Aβ signaling was inhibited.

Figure 5:
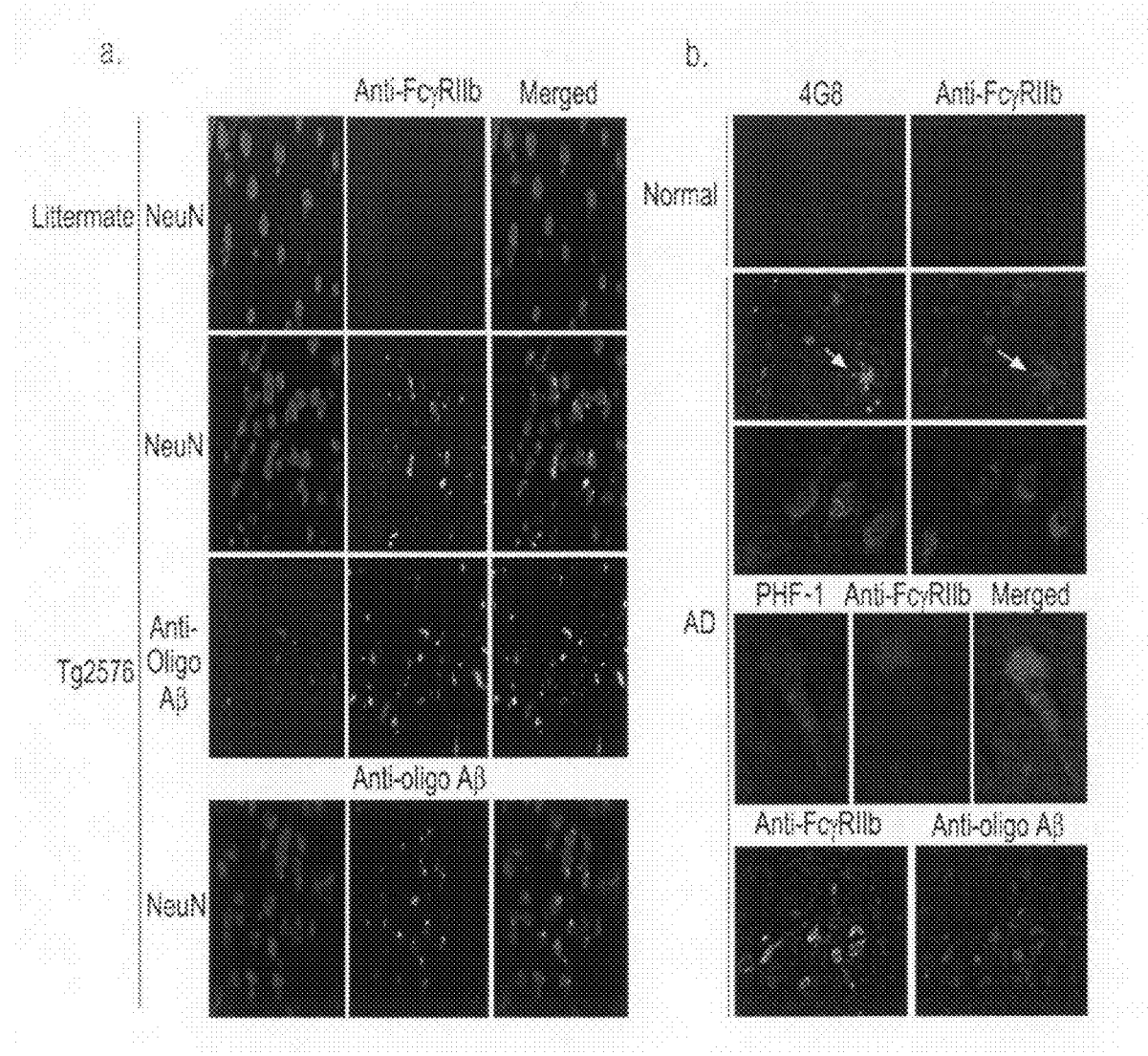
FIG. 5 shows the results of immunohistochemical analysis for FcγRIIb expression levels in the brains of Tg2576 mice (a) and AD patients (b)
Figure 6:
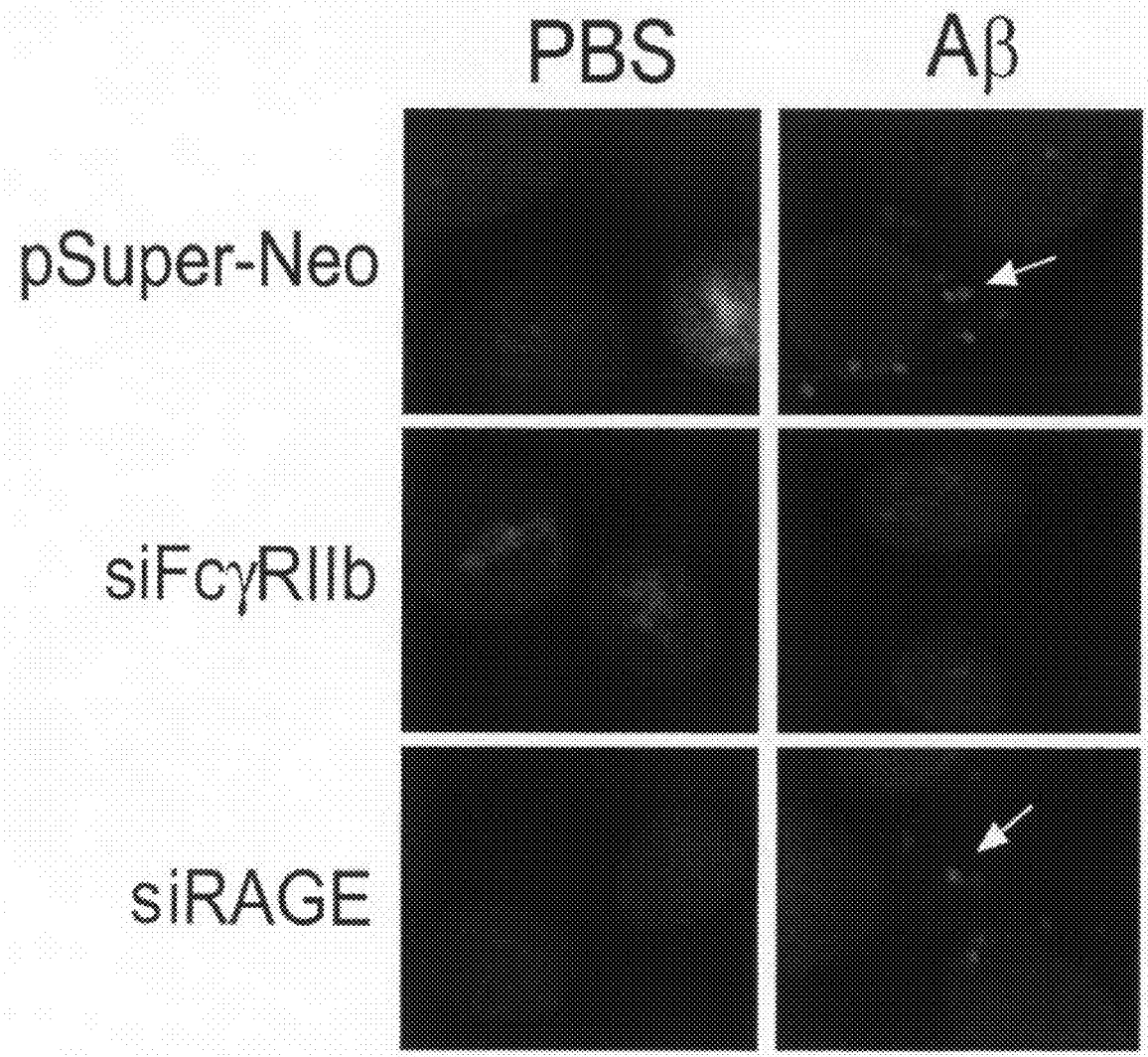
FIG. 6 shows the results of immunostaining for intracellular accumulation of $A\beta_{1-42}$ in siFcγRIIb-transfected cells.

The in vivo distribution of Aβ and FcγRIIb was examined. Oligomeric Aβ and FcγRIIb were found to be co-localized in the brain tissue of Tg2576 mice (AD animal model), indicating that both of them are present in the same region (FIG. 5a). Also, Aβ was expressed together with FcγRIIb in brain specimens from AD patients, confirming that both of them are present in the same cells (FIG. 5b). The transcriptional suppression of RAGE expression did not result in a decrease in the intracellular accumulation of Aβ, whereas the transcriptional suppression of FcγRIIb expression markedly reduced intracellular Aβ accumulation (FIG. 6). These results indicate that FcγRIIb is involved in the intracellular accumulation of Aβ as well as in intracellular signal transduction of Aβ.

Figure 7:
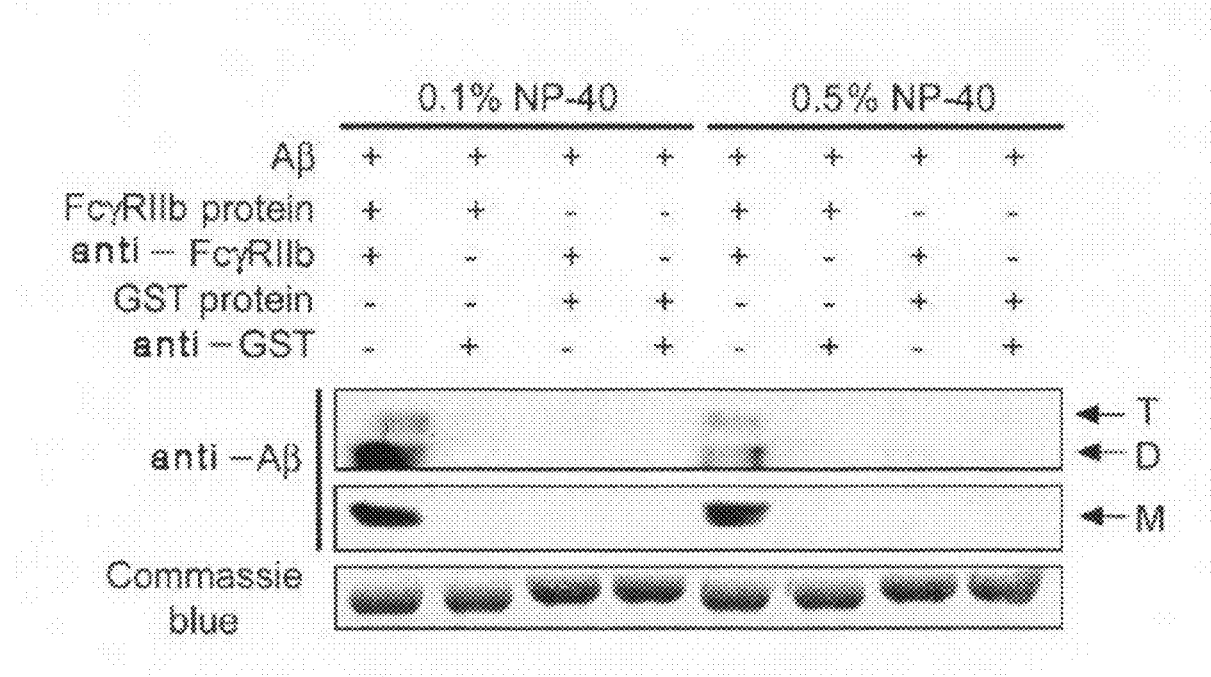
FIG. 7 shows the results of an in vitro binding assay between FcγRIIb and $A\beta_{1-42}$ (T: trimer; D: dimmer; M: monomer)

Based on the above results, the binding between Aβ and FcγRIIb was examined in vitro. The in vitro experiment revealed that Aβ binds to FcγRIIb (FIGS. 7 and 8).

Figure 9:
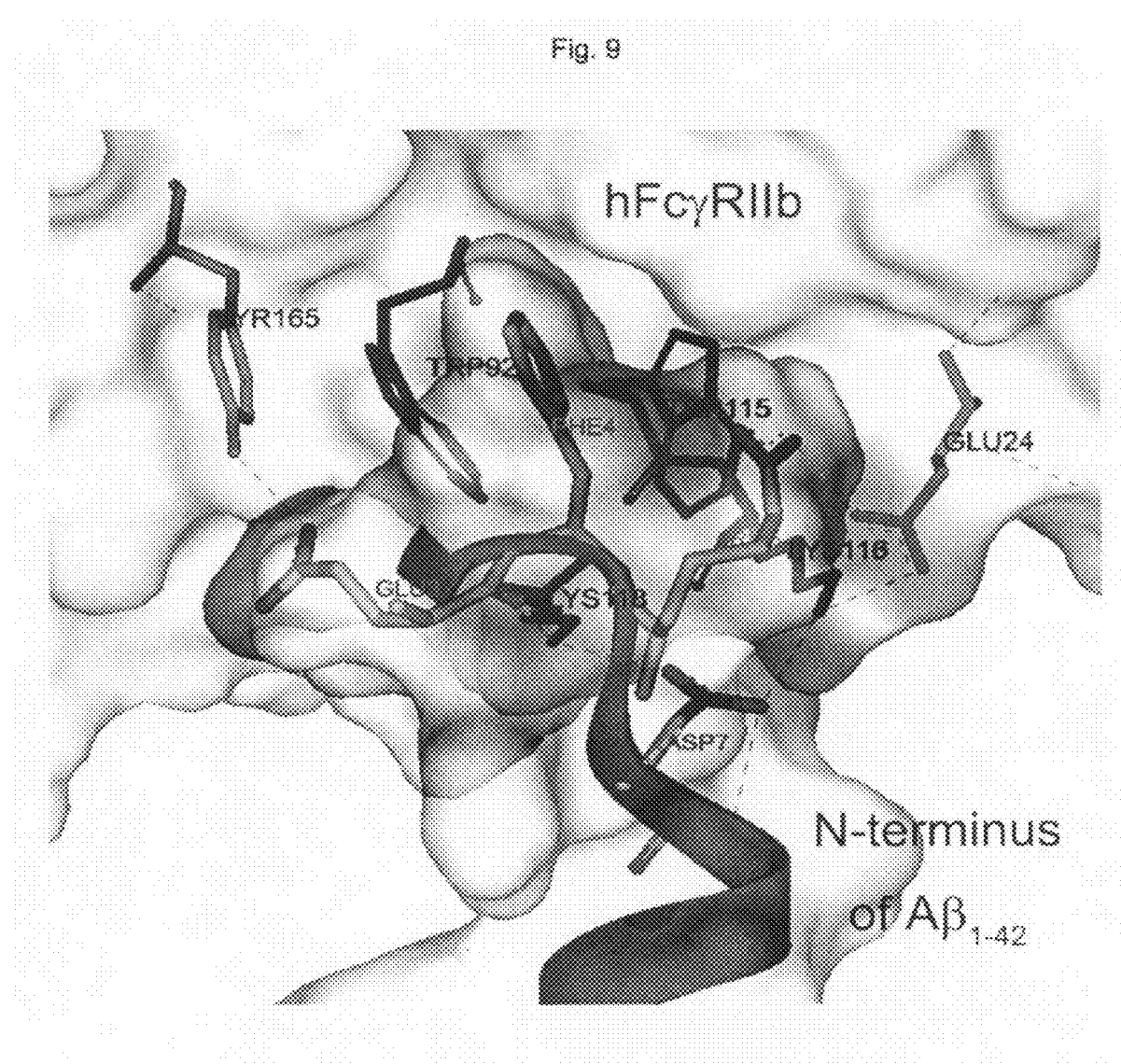
FIG. 9 showed the predicted binding site structure of $A\beta_{1-42}$ and FcγRIIb.

In addition, the inventors of this application identified for the first time the structure of Aβ bound to FcγRIIb using a computer program. Researchers made many efforts to determine the structure of Aβ, but failed to crystallize Aβ. Aβ is difficult to crystallize because it is present as amorphous aggregates, called amyloid plaques, in AD patients. However, recently, increasing evidence suggests that such Aβ aggregates are not directly involved in neuronal cell death, and that soluble oligomers of Aβ play a major role in neuronal toxicity. Recently, the three-dimensional structure of Aβ oligomers was determined by simulating the stable oligomerization of Aβ monomers using in silico methods (Urbanc, B. et al., Proc. Natl. Acad. Sci. U.S.A. 101, 17345-17350, 2004). The present inventors predicted the FcγRIIb-bound structure of Aβ using the known three-dimensional structures of Aβ and FcγRIIb. This predicted structure showed that the structures of Aβ and FcγRIIb precisely fit together (FIG. 9). Aβ binds to an extracellular domain of FcγRIIb. Aβ is present in oligomeric forms, in which hydrophilic N-terminal regions are flexible and C-terminal regions aggregate to form an oligomer. The present inventors found that extended N-terminal regions bind FcγRIIb to exert cytotoxicity using an affinity program (Insight II, Acelrys Co.).

When primary cultured neuronal cells from the cerebral cortex of rats were exposed to Aβ and treated with either IgG or IgA, Aβ neurotoxicity was blocked only in cultures treated with IgG, indicating that the Aβ binding site of FcγRIIb is identical to that for IgG. The co-crystal structure of Fcγ receptor IIIb, which has a structure similar to FcγRIIb, with IgG shows that a tryptophan pocket (Trp87 and Trp110) of FcγRIIIb interacts with a praline residue at 329 (Pro329) of IgG (Sondermann P. et al., Nature. 2000 Jul. 20; 406(6793): 267-273). As well, a peptide containing a tryptophan pocket of FcγRIIb has been shown to inhibit the binding between IgG and FcγRIIb (Goldsmith, E. B. et al., Biochemistry. 1997 Jan. 28; 36(4):952-959). Thus, the present inventors predicted the binding IgG and FcγRIIb also occurs in a tryptophan pocket (Trp92 and Trp115) and replaced two tryptophan residues (Trp92 and Trp115) of an FcγRIIb-CD40 chimeric protein with alanine. This replacement reduced NF-κB activation. The present inventors conducted an in silico simulation based on the above results. This simulation showed that a phenylalanine residue at position 4 of Aβ makes a strong hydrophobic interaction with two tryptophan residues, Trp92 and Trp115, of FcγRIIb, an aspartate residue at position 7 of Aβ makes a strong hydrophilic interaction with two lysine residues, Lys116 and Lys118, of FcγRIIb, a glutamine residue at position 3 of Aβ makes a relatively weak interaction with Tyr165 of FcγRIIb, and Arg5 and His6 residues of Aβ rarely interact with residues of FcγRIIb.

Figure 10:
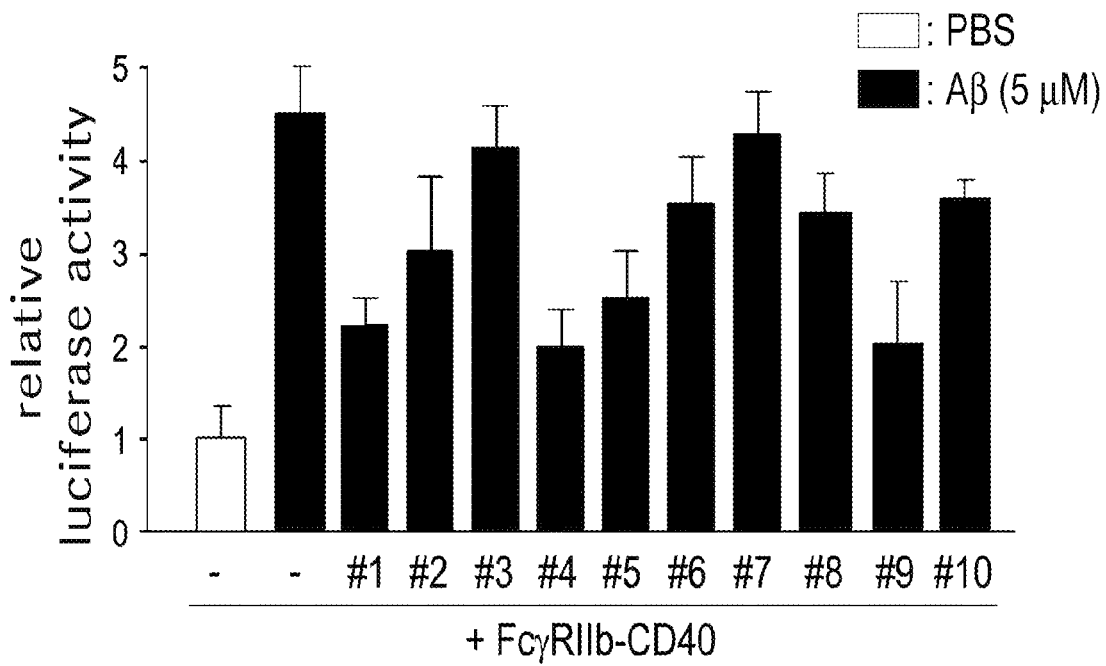
FIG. 10 shows the sequences of peptides inhibiting the binding between $A\beta_{1-42}$ and FcγRIIb (a) and the inhibition degree of the binding inhibitory peptides (b)
Figure 11:
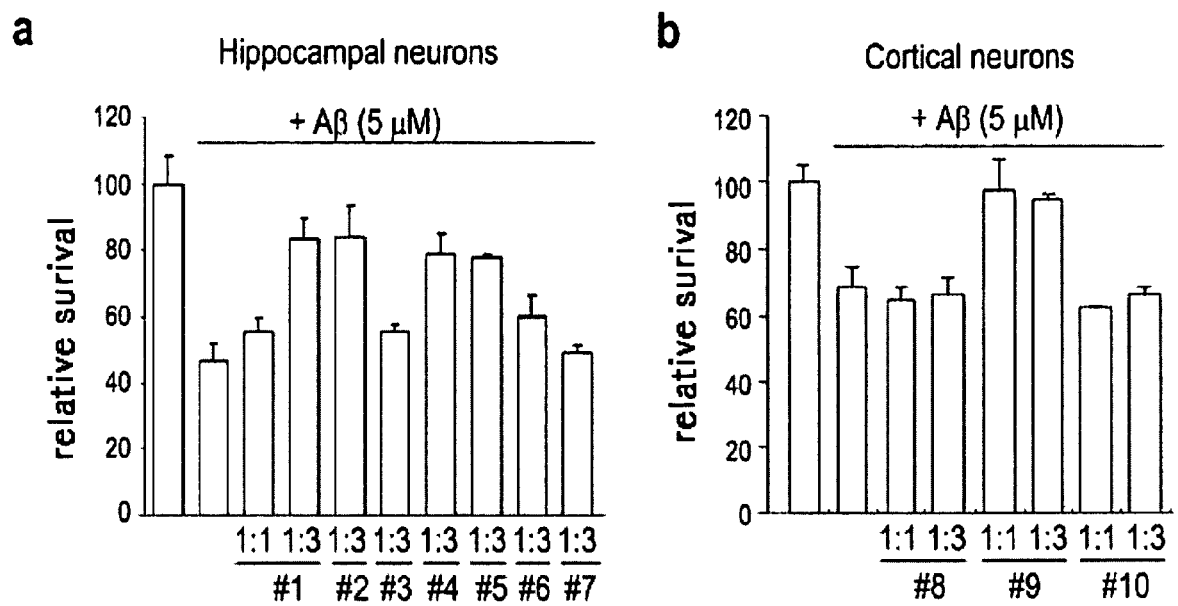
FIG. 11 shows the effects of the peptides inhibiting the binding between $A\beta_{1-42}$ and FcγRIIb on Aβ-induced neurotoxicity.

Based on the structure of Aβ bound to FcγRIIb, the present inventors prepared peptides capable of inhibiting the binding between Aβ and FcγRIIb. The peptides were found to effectively inhibit the binding between Aβ and FcγRIIb (FIGS. 10 and 11).

Figure 12:
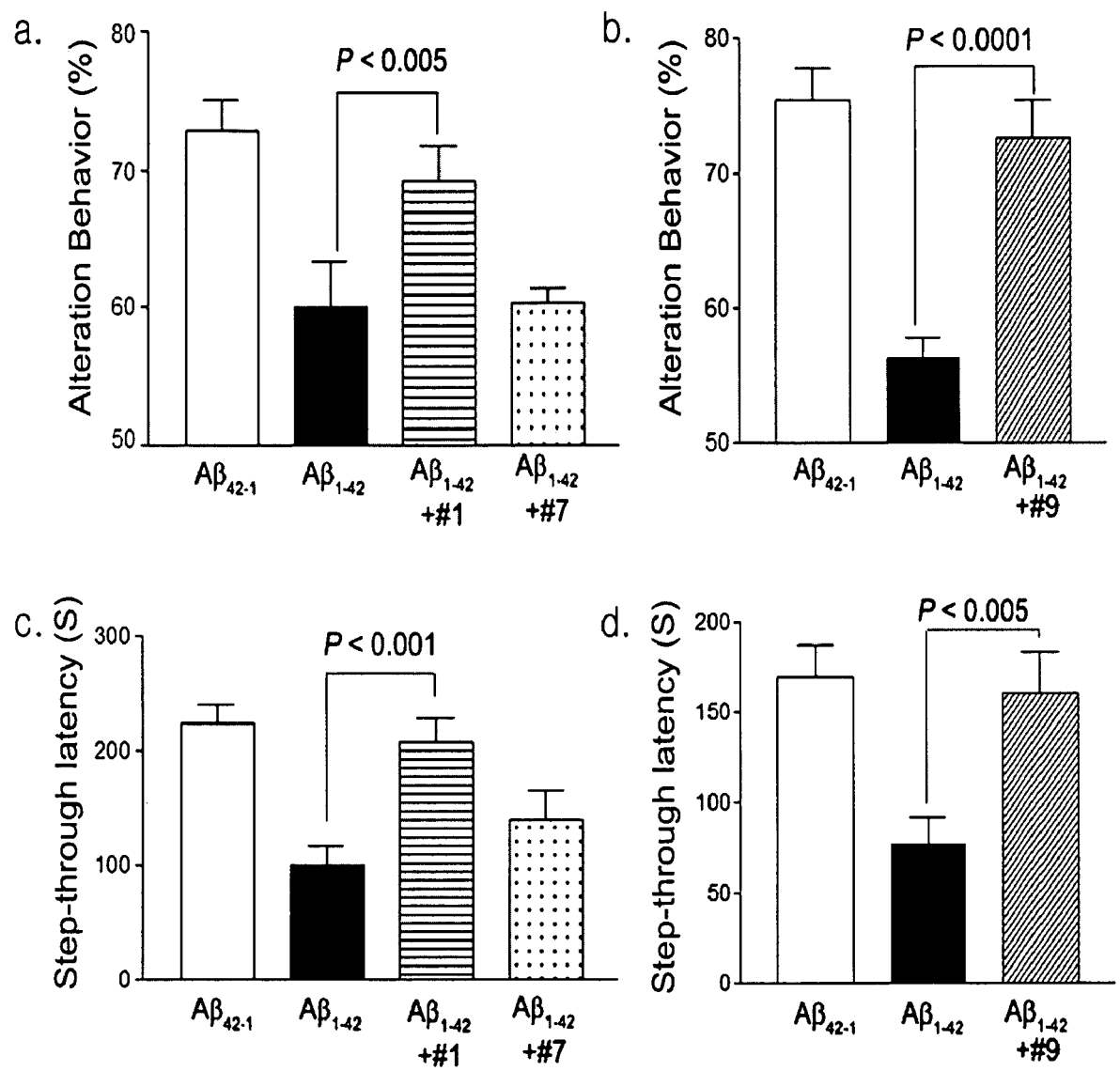
FIG. 12 shows the inhibitory effects of the peptides inhibiting the binding between $A\beta_{1-42}$ and FcγRIIb on memory decline (a and b: Y-maze test; c and d: passive avoidance test)

The peptides were injected into the brain of mice, and the memory ability of mice was assessed. As a result, memory impairment, as seen in AD cases, was remarkably restored (FIG. 12). Also, the mice treated with the peptide inhibitors displayed no accumulation of the full length $Aβ_{1-42}$ peptide in the brain (FIG. 13).

II. The Present Invention Provides Interaction Inhibitors Inhibiting the Interaction Between Aβ and FcγRIIb.

The interaction inhibitors may be selected from the group consisting of an FcγRIIb protein or a variant thereof, an FcγRIIb extracellular domain, an anti-FcγRIIb antibody, a peptide inhibiting the binding between Aβ and FcγRIIb, and an FcγRIIb expression inhibitor including an FcγRIIb-specific siRNA or an FcγRIIb-specific antisense nucleotide.

i) FcγRIIb Protein or Variant Thereof.

An FcγRIIb protein or a variant thereof competes with endogenous FcγRIIb in neuronal cells for Aβ binding to inhibit the binding of Aβ to endogenous FcγRIIb. Thus, a cell death signal of Aβ is not transduced into neuronal cells, thus preventing cell death.

The FcγRIIb protein has the nucleotide sequence of SEQ ID No. 30 and the amino acid sequence of SEQ ID No. 31, and variants thereof are also available. In a preferred embodiment, an FcγRIIb variant is prepared by replacing an isoleucine residue at 232 of human FcγRIIb with threonine, and has the sequence of SEQ ID No. 32. The variant is not specifically limited thereto, and any variant in which other residues of FcγRIIb are mutated and which is able to modulate the signal transduction mediated by FcγRIIb is available. In a preferred embodiment, when an FcγRIIb variant was prepared and introduced into neuronal cells, Aβ-induced neuronal cell death decreased (FIG. 2).

ii) FcγRIIb Extracellular Domain

FcγRIIb is composed of an extracellular domain and an intracellular domain, and the extracellular domain binds to Aβ. Thus, the extracellular domain also competes with endogenous FcγRIIb in neuronal cells for Aβ binding to thus inhibit the binding of Aβ to endogenous FcγRIIb, thereby inhibiting neuronal cell death.

The FcγRIIb extracellular domain may be any one derived from humans, mice, rats, or the like. Preferred is a human-derived extracellular domain of FcγRIIb. Also, the FcγRIIb extracellular domain may be produced using a method known to those skilled in the art, for example, through cloning into *E. coli*, mass production and purification, or through gene introduction into animal cells or other eukaryotic cells (yeast or insect cells) and purification. In the practice of the present invention, the FcγRIIb extracellular domain is purified using a method described in Sondermann P. et al., 1999 Mar. 1; 18(5):1095-1103. The FcγRIIb extracellular domain was found to increase the relative viability of neuronal cells exposed to Aβ to the same level as cells not exposed to Aβ (FIG. 4).

iii) Anti-FcγRIIb Antibody

An anti-FcγRIIb antibody, prepared using the entire region or extracellular domain of FcγRIIb as an antigen, competes with Aβ for FcγRIIb binding and thus inhibits the binding of Aβ to FcγRIIb in neuronal cells.

iv) Interaction Inhibitory Peptide

An interaction inhibitory peptides was prepared in order to inhibit the binding between Aβ and FcγRIIb. The peptide is designed based on an amino acid sequence predicted as a binding site of Aβ to FcγRIIb or vice versa (see FIG. 9), but is not limited thereto. Preferably, the peptide is a peptide or a mutant thereof, which consists of one to nine amino acids comprising phenylalanine at position 4 of SEQ ID No. 19, corresponding to the N-terminal region of Aβ. Also, preferably, the peptide is an amino acid, a peptide or a mutant thereof, which consists of one to nine amino acids, comprising tryptophan at position 5 of SEQ ID No. 27, spanning from position 107 to 114 of the amino acid sequence of FcγRIIb. In a preferred embodiment, peptides were designed to have sequences represented by SEQ ID Nos. 19 to 28, but are not limited thereto. When the specific peptides were incubated with FcγRIIb-CD40 chimera and Aβ, specific peptides #1, #4 and #9 effectively inhibited the binding between FcγRIIb-CD40 and Aβ (FIG. 10). When neuronal cells were treated with the peptides and Aβ, cells exhibited increased survival (FIG. 11). Also, the peptides were injected along with Aβ into the brains of mice, and mice were assessed for memory ability. Peptides #1 and #9 were found to restore Aβ-induced memory decline (FIG. 12). The immunohistochemical analysis of the brain of experimental animals showed that peptide #1 completely inhibited intracellular accumulation of Aβ in neuronal cells (FIG. 13).

v) FcγRIIb Expression Inhibitor

The term "FcγRIIb expression inhibitor" refers collectively to substances that specifically inhibit the transcriptional or translational expression of FcγRIIb, and may include siRNAs, antisense nucleotides and compounds.

FcγRIIb siRNAs are not limited to specific sequences, and any siRNA sequence capable of inhibiting the binding between Aβ and FcγRIIb by suppressing the expression of FcγRIIb may be used. In an embodiment, an FcγRIIb-specific siRNA consists of sense and antisense sequences, which are represented by SEQ ID Nos. 11 and 12. Sense and antisense sequences are suitably annealed and inserted into a pSuper-neo vector (Oligoengine, USA). A siRNA expression vector useful in the present invention is not specifically limited, but is preferably prepared by introducing a nucleotide sequence corresponding to the siRNA into a commonly used siRNA expression vector, psiRNA (Invitrogen, USA), PRNA (GenScript, USA), psLentGene (USA), pSIREN (Clontech, USA), pU6shX (VectorCoreA, Korea), pSilencer (aobion, USA), or pSuper-neo (Loigoengine, USA). The vector may be introduced into the nucleus of cells in the form of pure plasmid DNA or a complex with a transfection reagent or a target delivery substance, or in the form of a recombinant virus vector. Suitable viral vectors for use in the present invention include adenovirus, adeno-associated virus, and retrovirus including lentivirus. When the constructed vector was transfected into neuronal cells, it reduced Aβ-induced neuronal cell death (panel b, FIG. 3) and effectively inhibited intracellular Aβ (FIG. 6).

Antisense nucleotides have been approved as drugs having potential for therapeutic application to various human diseases. According to the Watson-Crick base pairing rules, a nucleotide is annealed to (hybridized with) a complementary sequence of DNA, immature mRNA or mRNA to interrupt the transmission of genetic information. The specificity of antisense nucleotides to target sequences makes them exceptionally multi-functional. An antisense-nucleotide is a long chain of monomer units and thus can be readily synthesized to correspond to a target RNA sequence. Many reports have recently demonstrated the usefulness of antisense nucleotides as a biochemical tool in the study of target proteins (Rothenberg et al., *J. Natl. Cancer Inst.*, 81:1539-1544, 1999). Many advances have been recently made in the fields of oligonucleotide chemistry and the synthesis of nucleotides having improved cell adhesion, target binding affinity and resistance to nucleases, suggesting that antisense nucleotides may be used in novel therapeutic approaches. For example, an antisense oligonucleotide targeting cmyb has been used to completely eliminate myelogenous leukemia cells from the bone marrow of patients suffering from myelogenous leukemia (Gewirtz and Calabreta, U.S. Pat. No. 5,098,890). Antisense nucleotides are known to have in vivo therapeutic efficacy on cytomegalovirus retinitis. Antisense nucleotides to FcγRIIb are not limited to specific sequences, but any antisense nucleotides inhibiting the binding between Aβ and FcγRIIb by suppressing the expression of FcγRIIb may be used.

III. The Present Invention Provides a Pharmaceutical Composition for Preventing or Treating AD Comprising the Interaction Inhibitor as an Effective Ingredient.

The present composition includes the effective ingredient in an amount of 0.0001 to 50 wt % based on the total weight of the composition.

In addition to the interaction inhibitor, the present composition may include one or more effective ingredients exhibiting functions that are the same as or similar to the interaction inhibitor.

The present composition may also include, in addition to the aforementioned effective ingredients, one or more pharmaceutically acceptable carriers for administration. The pharmaceutically acceptable carrier may include saline, sterile water, Ringer's solution, buffered saline, dextrose solution, maltodextrin solution, glycerol, ethanol, liposomes and mixtures of two or more thereof. If desired, the composition may further include other typical additives, such as antioxidants, buffers, and bacteriostatics. Also, diluents, dispersing agents, surfactants, binders and lubricants may be further added so as to be formulated into injectable formulations, such as solutions, suspensions and emulsions, pills, capsules, granules or tablets. The carrier may be conjugated to a target site-specific antibody or other ligands so as to act specifically in the target site. Further, the composition may be desirably formulated according to each disease or ingredient using a proper method in the art or the method described in Remington's Pharmaceutical Science (updated version, Mack Publishing Company, Easton Pa.).

The pharmaceutical composition of the present invention, although not limited thereto, is administered orally or parenterally (e.g., intravenously, subcutaneously, intraperitoneally or locally). The dosage may vary depending on the patient's weight, age, gender, health state and diet, administration time, administration mode, excretion rate, and severity of illness. The daily dosage ranges from about 0.01 to 12.5 mg/kg, and preferably from 1.25 to 2.5 mg/kg. The daily dosage may be taken as a single dose or divided into several doses.

IV. The Present Invention Provides a Method of Screening a Substance Inhibiting the Binding Between Aβ and FcγRIIb, FcγRIIb-Mediated Signal Transduction, or the Intracellular Translocation of Aβ and FcγRIIb.

i) The Present Invention Provides a Method of Screening an Inhibitor of the Interaction Between Aβ and FcγRIIb.

The screening method includes the steps of 1) adding a compound to be tested before, after or during the binding between all or part of FcγRIIb and all or part of Aβ; 2) measuring the binding degree between FcγRIIb and Aβ; and 3) determining whether the compound reduces the binding between Aβ and FcγRIIb in comparison with a control. At step 1), the entire FcγRIIb protein may have the sequence of SEQ ID No. 31, and the partial portion of FcγRIIb may be an FcγRIIb extracellular region which is represented by SEQ ID No. 33. The entire Aβ protein may have the sequence of SEQ ID No. 29, and the partial portion of Aβ may be an N-terminal region of Aβ. The screening may be carried out using various methods analyzing protein-protein interaction, which are known to those skilled in the art. Such methods for analyzing the association between proteins include yeast two-hybrid system (Parda et al., *Epub*, 85:347-355, 2005), immunoprecipitation (IPP), Biocore™, Fluorescence Energy Transfer (FRET), and GST-full down assay (Lee S Y, *Biochem Biophys Res Commun*, 334:1445-1451, 2005), but the present invention is not limited thereto, and any known methods for analyzing the association between proteins may be used.

ii) The Present Invention Provides a Method of Screening an Inhibitor of FcγRIIb.

The screening method includes the steps of 1) contacting all or part of FcγRIIb with a compound to be tested; 2) measuring the binding degree of the compound to FcγRIIb; and 3) determining whether the compound has high binding affinity to FcγRIIb in comparison with a control. At step 1), the entire FcγRIIb protein may have the sequence of SEQ ID No. 31, and the partial portion of FcγRIIb may be an FcγRIIb extracellular region, which is represented by SEQ ID No. 33. The screening may be carried out using various methods analyzing protein-compound interaction, which are known to those skilled in the art. Such methods include MALDI-TOF, but the present invention is not limited thereto, and any known methods for analyzing the association between a protein and a compound may be used.

iii) The Present Invention Provides a Method of Screening a Substance Inhibiting the Expression of FcγRIIb.

The screening method includes the steps of 1) treating a brain cell culture with a compound to be tested; 2) measuring the expression level of FcγRIIb in the brain cell culture; and 3) determining whether the compound inhibits FcγRIIb expression in comparison with a control. At step 1), B103 cells or primary neuronal cells from the cerebral cortex may be used, but the present invention is not limited thereto, and any known cell lines expressing FcγRIIb may be used. The FcγRIIb expression may be assessed using RT-PCR, an immunoassay, and the like, but the present invention is not limited thereto, and any known methods for measuring the amount of a transcript or a protein translated therefrom may be used.

iv) The Present Invention Provides a Method of Screening a Substance Inhibiting the Intracellular Translocation of Aβ and FcγRIIb.

The screening method includes the steps of 1) treating a brain cell culture with Aβ and a compound to be tested; 2) detecting the intracellular level of Aβ in the brain cell culture; and 3) determining whether the compound inhibits the intracellular translocation of Aβ in comparison with a control. At step 1), B103 cells or primary neuronal cells from the cerebral cortex may be used, but the present invention is not limited thereto and any known cell lines expressing FcγRIIb may be used. The intracellular translocation of Aβ may be assessed using antibodies, compounds and peptides binding specifically to Aβ or FcγRIIb. Also, Aβ and FcγRIIb may be detected using a protein conjugated to a fluorescent, colorimetric or radioactive protein, compound or peptide. Thus, Aβ and FcγRIIb may be detected using fluorescence detection, radioactive detection and colorimetric detection apparatuses.

v) The Present Invention Provides a Method of Screening a Substance Inhibiting the Interaction Between Aβ and FcγRIIb Using an FcγRIIb Chimeric Protein.

The screening method includes the steps of 1) treating a cell line expressing an FcγRIIb chimeric protein with Aβ and a compound to be tested; 2) measuring the activity of the FcγRIIb chimeric protein; and 3) determining whether the compound inhibits the activity of the chimeric protein in comparison with a control. At step 1), the FcγRIIb chimeric protein is a receptor, and any protein capable of measuring the force of interaction between Aβ and FcγRIIb, as determined through the expression, color development or color change thereof, or the cellular signal transduction mediated thereby, may be fused to FcγRIIb. The FcγRIIb chimeric protein may be created by linking FcγRIIb to a specific protein, of which the expression, color development, color change or cellular signal transduction is stimulated upon the interaction between FcγRIIb and Aβ. In a preferred embodiment, CD-40, activating cellular signal transduction, was linked to FcγRIIb. In the present invention, the transmembrane protein CD-40 mediating intracellular signal transduction was used, but a protein such as TRK, which contains both a transmembrane domain and a cytoplasmic domain, is preferred. However, the present invention is not limited thereto.

vi) The Present Invention Provides a Method of Screening a Substance Inhibiting the Interaction Between Aβ and FcγRIIb Using a Software Program.

The screening method includes the steps of 1) inputting information about the structure of a compound to be tested into a software program; and 2) determining whether the compound inhibits the binding between Aβ and FcγRIIb using the software program. The software program useful in the method may be selected from the group consisting of DOCK™, FlexX™, and Affinity™. The present inventors employed an Affinity Program (InsightII, Accelrys Inc). A compound inhibiting Aβ-FcγRIIb interaction may be determined based on 1) the protein structure of FcγRIIb, containing amino acids corresponding to glutamic acid at position 64, tryptophan at 132, tryptophan at 155, lysine at 156 and lysine at 158 of SEQ ID No. 31, and 2) the protein structure of Aβ, containing amino acids corresponding to glutamic acid at position 3, phenylalanine at 4, histidine at 6 and aspartic acid at 7 of SEQ ID No. 29.

V. The Present Invention Provides a Method of Diagnosing Alzheimer's Disease by Measuring the Expression Level of FcγRIIb.

The expression level of FcγRIIb may be detected using any known methods capable of measuring the expression level of the FcγRIIb protein. Examples of such methods include, but are not limited to, an immunoassay with an antibody binding specifically to FcγRIIb, and RT-PCR and Northern blotting with nucleic acid molecules capable of complementarily binding to the FcγRIIb gene.

X. The Present Invention Provides a Kit for Diagnosing Alzheimer's Disease by Measuring the Expression Level of FcγRIIb.

The diagnostic kit may include DNA, RNA and a protein, binding specifically to FcγRIIb, a buffer, a standard antibody, a secondary antibody labeled with an enzyme catalyzing a colorimetric reaction or a fluorescent substance, and a substance for color development. Also, when a compound binding specifically to FcγRIIb is used, this compound is used in a form in which it is conjugated to a fluorescent or colorimetric label, which may be visually detected.

The present invention also provides a method of diagnosing Alzheimer's disease using the diagnostic kit. The method includes the steps of 1) collecting a specimen from a subject; 2) reacting the specimen with a substance binding specifically to FcγRIIb and washing the specimen; and 3) measuring the amount of the specifically bound substance. At step 3), when an antibody specific to FcγRIIb is used, the antibody is allowed to react with a secondary antibody conjugated to a fluorescent substance, is washed, and is analyzed using a fluorescence microscope or scanner. When a compound specific to FcγRIIb is used, the bound compound may be quantified in a bound or separated state.

A better understanding of the present invention may be obtained through the following examples which are set forth to illustrate, but are not to be construed as the limit of the present invention.

Example 1

Gene Expression Profiling Using DNA Microarray

Neuronal cells were isolated from the cerebral cortex of 16 day-old rat embryos and cultured. The primary-cultured cortical neuronal cells were exposed to 5 μM of Aβ (500 μM in PBS; Sigma, USA) for 24 hrs. Total RNA was isolated from the cells using TRIZOL Reagent (GIBCO-BRL, USA) according to the manufacture's protocol. Gene expression was analyzed using DNA microarray filters (GF300, GF301, GF302, Invitrogen, USA) containing 17,000 rat cDNAs according to the manufacturer's instruction. Results obtained from three independent experiments were statistically analyzed using the Pathway3™ software program (Resgen™, Invitrogen, USA).

As a result, the expression of FcγRIIb exhibited a 2.740.5-fold increase compared to control DNA spots (consisting of total genomic DNA). Through this DNA microarray analysis, the increased expression of E2-25K/Hip-2 and changes in the expression of other proteins of the ubiquitin/proteasome system were previously reported (Song et al., *Molecular cell*, 12(3), 553-563, 2003).

Example 2

Detection of Changes in FcγRIIb Expression Upon Exposure to Aβ

2-1: Reverse Transcription Polymerase Chain Reaction (RT-PCR)

The primary neuronal cells from the rat cerebral cortex were exposed to 5 μM of Aβ for 48 hrs. Cells were harvested, and total RNA for reverse transcription was isolated using TRIZOLR Reagent (Invitrogen, USA). cDNAs were synthesized through reverse transcription, which was carried out using 5 μg of total RNA and ImProm-II™ Reverse Transcriptase (Promega, USA) according to the manufacturer's protocol. RT-PCR was performed using the following primers: FcγRIIb-5'-EcoRI primer (5'-CGCGGAATTCGATG-GACAGCAACAGGACT-3': SEQ ID No. 1), FcγRIIb-3'-KpnI primer (5'-CGGGTACCATAATGTGGTT CTGGTAGTC-3': SEQ ID No. 2), FcγRI-RT-5' primer (5'-TTGGTGAACACAGTTCTCTATGT-GAAAATACACAGGCTGC-3': SEQ ID No. 3), FcγRI-RT-3' primer (5'-CTATCTTACAGTGGCTGTTACTTCT-TCATACACGTCATCGCT-3': SEQ ID No. 4), FcγRIIa-RT-5' primer (5'-GCCGATTTCTGCCTAGTGATGTGCCTC-CTGTTTGCAGTGG-3': SEQ ID No. 5), and FcγRIIa-RT-3' primer (5'-TCATTTGTCCTGTGGAGCCTCTTTC-CGACTGACAGGGATC-3': SEQ ID No. 6). β-actin was used as an internal control, and was amplified with the β-actin sense primer (5'-GCGTCCACCCGCGAG-3': SEQ ID No. 7) and the β-actin anti-sense primer (5'-TATAGCAGGGT-CAAC-3': SEQ ID No. 8). PCR was carried out in a total volume of 50 μl using one-fifth of the reverse transcription reaction solution as a template. PCR conditions included denaturation at 95° C. for 5 min, and 10, 15, 20 or 25 cycles of denaturation at 95° C. for 60 sec, annealing at 56° C. for 60 sec and extension at 72° C. for 60 sec, followed by final extension at 72° C. for 7 min.

The exposure of B103 cells to Aβ resulted in a specific increase of FcγRIIb expression (panel a, FIG. 1). These results were consistent with those of the DNA microarray analysis in Example 1.

2-2. Western Blot Analysis

Rat B103 neuronal cells were treated with a calcium chelator (BAPTA-AM, 5 μM; EGTA, 1 mM), a calpain protease inhibitor (calpeptin, 10 μM), and an antioxidant (ascorbic acid, 5 μM) for 2 hrs, and exposed to Aβ for 48 hrs. Then, cells were lysed with a sampling buffer (10% glycerol, 2% SDS, 62.5 mM Tris-HCl, 2% β-mercaptoethanol, pH 6.8). The cell lysates were separated on a 12% sodium dodecyl sulfate polyacrylamide gel electrophoresis (SDS-PAGE) gel, and transferred onto a nitrocellulose membrane. Western blotting was performed with the primary antibody, monoclonal K9.631 (a gift from Dr. Hammerling, Memorial Sloa Kettering Cancer Center, NY) and goat anti-mouse IgG antibody-conjugated horseradish peroxidase as a secondary antibody (Santa Cruz Biotechnology, USA). A control was incubated with anti-α-tubulin antibody (T5168) (Sigma, USA) and the same HRP-conjugated secondary antibody.

The Western blotting showed that the Aβ-induced FcγRIIb expression was not suppressed upon treatment with the calcium chelators, calpain protease inhibitor and antioxidant (panel, FIG. 1). Thus, the Aβ-induced FcγRIIb expression seems to occur in a specific manner. Also, the FcγRIIb expression increased even upon the blocking of the action of calcium and active oxygen species, which mediate the toxic signaling of Aβ, indicating that Aβ acts upstream of Aβ signaling to induce FcγRIIb expression.

2-3. Immunostaining

As described in Example 2-1, B103 cells were exposed to PBS, tunicamycin (Tuni), which inhibits N-glycosylation as post-translational modification of proteins, and Aβ for 48 hrs. Cells were fixed, probed with the primary antibody monoclonal K9.631 (Memorial Sloa Kettering Cancer Center, NY), and observed under a fluorescence microscope (Leica DMRBE, Germany). This test was carried out as described in Song et al., *Molecular cell*, 12(3), 553-563, 2003.

When B103 cells were exposed to Aβ, the expression of FcγRIIb increased (panel c, FIG. 1). These results were consistent with those of the DNA microarray analysis in Example 1.

Example 3

Evaluation of Cell Death Upon FcγRIIb Overexpression and Inhibition of Aβ Neurotoxicity Using FcγRIIb Mutant

An FcγRIIb expression vector and an FcγRIIb mutant expression vector were constructed and transfected into rat neuronal B103 cells. The expression vectors were prepared as follows. The rat FcγRIIb gene was amplified by performing PCR using a rat brain cDNA library (Invitrogen, USA) as a template with a set of FcγRIIb-5'-EcoRI primer (5'-CGCG-GAATTCGATGGACAGCAACAGGACT-3': SEQ ID No. 1) and FcγRIIb-3'-KpnI primer (5'-CGGGTACCATAATGTG-GTTCTGGTAGTC-3': SEQ ID No. 2). PCR was carried out in a total volume of 100 μl using 20 pmol of each primer. PCR conditions included denaturation at 95° C. for 5 min, and 30 cycles of denaturation at 95° C. for 60 sec, annealing at 56° C. for 60 sec and extension at 72° C. for 60 sec, followed by final extension at 72° C. for 7 min. The amplified rat FcγRIIb gene was inserted into pEGFP-N1 (Clonetech, USA), and the resulting vector was designated "pFcγRIIb". An FcγRIIb (I232T) mutant was prepared through PCR using FcγRIIb [I232T]-5' primer (5'-GCTGTCGCTGGAACTGTAGCT-GCC-3': SEQ ID No. 9) and FcγRIIb [I232T]-3' primer (5'-GGCAGCTACAGCAGTTCCAGCGACAGC-3': SEQ ID No. 10).

PCR was carried out in a total volume of 50 μl using 10 pmol of each primer. PCP conditions included denaturation at 95° C. for 5 min, and 30 cycles of denaturation at 95° C. for 5 min, annealing at 56° C. for 60 sec and extension at 72° C. for 10 sec, followed by final extension at 72° C. for 30 min. The amplified rat FcγRIIb[I232T] mutant gene was inserted into pEGFP-N1 (Clonetech, USA), and the resulting vector was designated "pFcγRIIb[I232T]". This vector was digested with DpnI, and the excised mutant gene was subjected to DNA sequencing, which was performed by the COSMO Company (Korea). Then, B103 cells were transfected with 300 ng of PEGFP, 900 ng of pcDNA3 (void vector), 900 ng of pFcγRIIb, and 900 ng of pFcγRIIb[I232T] using lipofectamine (Invitrogen, USA) according to the manufacturer's instructions. Cells were then exposed to 5 μM of Aβ and phosphate buffered saline (PBS) for 48 hrs. Cell viability was estimated under a fluorescence microscope based on the morphology of green fluorescent protein (GFP)-positive cells (expressing GFP through pEGFP introduction).

FcγRIIb-overexpressing B103 cells exhibited increased cell death, whereas neuronal cell death was inhibited in B103 cells transfected with the FcγRIIb mutant expression vector (FIG. 2). These results indicate that Aβ signaling occurs via FcγRIIb, and that an FcγRIIb mutant is useful to inhibit the toxic signaling of Aβ.

Example 4

Construction of siRNAs Specific to FcγIIb and RAGE

Small interfering RNAs (siRNAs) inhibiting the expression of FcγIIb and receptors for advanced glycation end-product (RAGE), which is known as a cell surface receptor of Aβ, were constructed, and their effects on cell death were compared to each other. A siRNA duplex was formed by hybridizing sense and antisense complementary RNA oligo-nucleotides, listed in Table 1, below, and was inserted into pSuper-neo (Oligoengine, USA). The siRNA expression vectors thus constructed were individually transfected into B103 cells using lipofectamine (Invitrogen, USA) according to the manufacturer's protocol. The resulting transfected cells were designated "pSuper-neo", "psiFcγRIIb#1", "psiFcγRIIb#2", "psiRAGE#1", and "psiRAGE#2". Then, transfected cells were subjected to Western blot analysis. Western blotting was performed as described in Example 2-2 with anti-FcγRIIb antibody (primary antibody K9.361; secondary antibody: goat anti-mouse IgG conjugated to horseradish peroxidase (Santa Cruz Biotechnology, USA)), anti-RAGE antibody (primary antibody: Sc8230 (Santa Cruz Biotechnology, USA); secondary antibody: donkey anti-goat IgG conjugated to horseradish peroxidase (Santa Cruz Biotechnology, USA)), and anti-α-tubulin antibody (primary antibody: T5168 (Sigma, USA); secondary antibody: goat anti-mouse IgG conjugated to horseradish peroxidase (Santa Cruz Biotechnology, USA)). As a result, siRNAs were found to completely suppress the expression of FcγRIIb and RAGE (panel a, FIG. 3). Then, the transformed B103 cells were exposed to 5 μM of Aβ or PBS for 48 hrs, and their viability was evaluated. Cell survival was assessed through trypan blue exclusion, Hoechst staining (Sigma, USA), and Annexin V labeling (Promega, USA). The survival of effector cells and cells introduced with pEGFP (Clontech, USA) was determined by observing the morphology of GFP-positive cells under a fluorescence microscope (Leica DMRBE, Germany). Cells were determined to be dead when the cell morphology changed to a spherical shape and the cell membrane was disrupted or destroyed.

Cell death was blocked in cells transfected with a siRNA against FcγRIIb. In contrast, cells transfected with a siRNA against RAGE, which is known to be a receptor of Aβ, exhibited low survival (panel b, FIG. 3). That is, a siRNA against RAGE, which is known as a target for inhibiting Aβ signaling, was found to have a poor inhibitory effect on neuronal cell death, whereas the silencing of FcγRIIb expression was found to eliminate Aβ signaling.

TABLE 1

RNA oligonucleotides for siRNA construction

|  | Sequence | SEQ ID No. |
|---|---|---|
| siFcRb-5'-sense oligomer | 5'-GATCCCCTCGGAGAGCCACTTATGCTTTC AAGAGAAGCATAAGTGGCTCTCCGATTTTTGG AAA-3' | 11 |
| siFcRb-3'-antisense oligomer | 5'-AGCTTTTCCAAAAATCGGAGAGCCACTTA TGCTTCTCTTGAAAGCATAAGTGGCTCTCCCG AGGAGTCGGG-3' | 12 |
| siRAGE-5'-sense oligomer | 5'-GATCCCCGCTCCGGATGAAGAATCAGTTC AAGAGACTGATTCTTCATCCGGAGCTTTTGG AAA-3' | 13 |
| siRAGE-3'-sense oligomer | 5'-ACCTTTTCCAAAAAGCTCCGGATGAAGAA TCAGTCTCTTGAACTGATTCTTCATCCGGAGC GGAGTCGGG-3' | 14 |

Example 5

The Effect of FcγRIIb Extracellular Domain (ED) on Neuronal Cell Death

An FcγRIIb extracellular domain (ED) was purified as described in Sondermann et al., *EMBO J*, 18:1095-1103, 1999. Neuronal B103 cells or primary-cultured neuronal cells were exposed to 5 μM of Aβ for 48 hrs. Then, cells were treated or not treated with 100 μg of the purified FcγRIIb ED, or treated or not treated with 100 μg of bovine serum albumin (BSA). B103 cells were subjected to Western blotting, which was performed with anti-FcγRIIb antibody as described in Example 2-2. The primary neuronal culture was evaluated for cell survival as described in Example 3.

Compared to BSA treatment, the FcγRIIb ED was found to completely inhibit Aβ signaling in Aβ-exposed cells (FIG. 4), indicating that the FcγRIIb ED is an extracellular receptor of Aβ. Thus, the FcγRIIb ED may have potential as a target for inhibiting the neurotoxic signaling initiated by Aβ.

Example 6

Immunohistochemical Assay

The transgenic mouse used in this test was Tg2576 (18 to 24 months old, female), which contained the human APP695 with the double mutation Lys670→Asn and Met671→Leu (K670N, M671L), which was found in a large Swedish family suffering from the early onset of Alzheimer's disease (Hsiao et al., Science, 274:99-102, 1996). The mouse was anesthetized with 7% chloral hydrate, and perfused transcardially with 4% phosphate-buffered paraformaldehyde (PFA; Sigma, USA). For neuropathological analysis, the brain was excised and immersed in PFA for 48 hrs. Then, the brain was cut into serial coronal sections on a freezing microtome. The sections were mounted on glass slides, dried, and fixed again with 4% PFA for 15 min. The sections were incubated in methanol, containing 3% $H_2O_2$ for 5 min, to remove endogenous peroxidase activity. Then, the brain sections were washed, immersed in 0.5% Triton X-100 for 30 min before being reacted with the primary antibody, and incubated with 1% bovine serum albumin for 1 hr.

Specimens from fifteen patients neuropathologically diagnosed as having AD (71 to 93 years of age; 83.83 years old on average; corpse dissection 2 to 16 hrs after death) were donated from McLean Hospital (Harvard Brain Tissue Resource Center, Belmont, Mass.) and Ohio state university (Columbus, Ohio). All tissues were confirmed through clinical records and neuropathological examinations.

Mouse brain sections and immunofluorescent-labeled brain sections from AD patients were observed under a fluorescence microscope (Leica DMRBE, Germany). Subsequently, brain sections were stained with an alkaline Congo red solution (Sigma, USA). Tg2576 mouse samples were stained with anti-oligo-Aβ antibody (Biosource, USA), NeuN (Chemicon, USA), and anti-FcγRIIb antibody (K9.361, gift from Dr. Hammerling, Memorial Sloa Kettering Cancer Center, NY; or rabbit polyclonal Antibody, gift from Dr. Cambier, University of Colorado Health Sciences Center, CO). AD patient samples were stained with anti-Aβ monoclonal antibody (4G8:Signet, USA), anti-PHF-1 antibody (gift from Dr. Davis, Albert Einstein College of Medicine, NY).

Both amyloid plaques (asterisk) and FcγRIIb immunoreactivity (arrowheads) were detected in the brains of AD patients. Also, strong immunoreactivity was observed within neuronal cells (right panels (b), FIG. 5). FcγRIIb was found to be strongly accumulated within neuronal cells and localized along with oligo-Aβ (FIG. 5). The strong increase of FcγRIIb in AD patients may be used in AD diagnosis. Also, these results demonstrate that FcγRIIb contributes to intraneuronal Aβ accumulation, indicating that FcγRIIb contributes to the intraneuronal accumulation of Aβ as well as the signaling ability of Aβ.

Example 7

Evaluation of Intracellular Aβ Accumulation in B103 Cells Transfected with siRNA Expression Vectors psiFcγRIIb #1 cells or psiRAGE #1 cells, prepared in Example 4, were exposed to 100 nM of Aβ or PBS for 12 hrs, and immunostained with anti-Aβ antibody (4G8; Signet, USA) according to the same method as in Example 2-3.

Intracellular Aβ accumulation was strongly inhibited in psiFcγRIIb cells but was maintained in psiRAGE cells, indicating that FcγRIIb mediates the intracellular accumulation of Aβ in neurons (FIG. 6). Thus, psiFcγRIIb of FcγRIIb mutants may be useful in inhibiting intraneuronal Aβ accumulation.

Example 8

In Vitro Assay for the Binding Between FcγRII and $A\beta_{1-42}$

5 μM of Aβ was mixed with 20 μg of FcγRIIb-ED or 20 μg of BSA in vitro, and was incubated at 37° C. for 3 hrs. The reaction mixture was incubated with anti-FcγRIIb polyclonal antibody or anti-GST antibody for 2 hrs, and then with Protein G for 3 hrs (binding solution: 50 mM Tris-HCl, pH 7.4, 1 mM DTT, 0.5 mM EDTA, 0.01% Triton X-100, 0.5 mg/ml bovine serum albumin, 10% (v/v) glycerol, protease inhibitors cocktail, several concentrations of NP-40). The beads were washed three times and subjected to Western blotting to assess the association between FcγRII and $A\beta_{1-42}$. Western blotting was carried out with K9.361 antibody and anti-Aβ antibody (primary antibody: 71-5800 (Zymed, USA); secondary antibody: goat anti-rabbit IgG conjugated to horseradish peroxidase (Santa Cruz Biotechnology, USA).

Aβ was found to directly bind to FcγRIIb-ED (FIG. 7). These results indicate that FcγRIIb is a receptor of Aβ and is thus useful in analysis for extracting inhibitors of the binding.

Example 9

Evaluation of the Binding Between FcγRIIb-CD40 Chimera and Aβ

In order to investigate whether FcγRIIb binds to Aβ in a specific manner, an extracellular domain of FcγRIIb was genetically fused to CD40, consisting of a transmembrane domain and a cytoplasmic domain. The resulting FcγRIIb-CD40 fusion gene was expressed in NIH3T3 cells to increase NF-κB activity, a signal transducer of CD40, when the fusion protein binds to Aβ. The chimeric gene was constructed as follows. A rat FcγRIIb extracellular region and human CD40 transmembrane and cytoplasmic domains were amplified by performing PCR with FcγRIIb-ED-5'-NheI primer (5'-GCTAGCGCTATGGACAGCAACAGGACT-3': SEQ ID No. 15), FcγRIIb-ED-3'-HindIII primer (5'-AAGCTTGG-GAGGCAACGAACTGCTGGATTT3': SEQ ID No. 16), CD40-TM+cyto-5' primer (5'-CCCAAGCTTGGGGC-CCTGGTGGTGATCCCCATC-3': SEQ ID No. 17), and CD40-TM+cyto-3' primer (5'-CGGGTACCATTCACT-GTCTCTCCTGCAC-3': SEQ ID No. 18). PCR products were inserted into a pEGFP-N1 vector according to the same method as in Example 3. Cells were transfected with the chimeric gene, CD40, TNFRI, pcDNA3 (mock) along with an NF-kB-luciferase gene, and were exposed to 5 μM of Aβ or 20 ng/ml of TNF. NF-κB activity was assessed, as described in Woo et al., *FEBS Lett.* 578, 239-244, 2004.

When cells were exposed to Aβ, CD40 did not stimulate NF-κB activity, but FcγRIIb-CD40 strongly stimulated NF-κB activity (FIG. 8). These results indicate that Aβ binds specifically to FcγRIIb to form a complex, which is capable of triggering signal transduction.

Example 10

Prediction of the Binding Structure of FcγRIIb and Aβ

In recent years, it has become apparent that Aβ accumulated in an irregularly aggregated form or in a fibrillar form does not cause signal transduction of neurotoxicity, but soluble oligomers of five or six Aβ monomers initiate neurotoxic signaling and stimulate memory decline (Cleary, J. P. et al. *Nat. Neurosci.* 8:79-84, 2005). The Aβ monomer is difficult to crystallize, and structure thereof is difficult to determine, due to its tendency to aggregate. For this reason, the structure of soluble oligomeric Aβ was predicted through computational analysis. A computational study revealed the assembly of Aβ monomers into a globular soluble oligomeric structure, in which N-terminal tails are exposed to the exterior and C-terminal hydrophobic regions aggregate to form an oligomer (Urbanc, B. et al. *Proc. Natl. Acad. Sci. U.S.A.* 101:17345-17350, 2004). Also, the N-terminal structure of oligomers was similar to that of monomeric Aβ. In this regard, the inventors of this application predicted that FcγRIIb binds the N-terminal region of Aβ, and identified first the binding site structures between FcγRIIb and Aβ using the N-terminal structure of Aβ, which was determined through a nuclear magnetic resonance (NMR) study of a computational prediction method (AffinityR program: InsightII, Accelrys Inc). The structures of the binding regions in FcγRIIb and Aβ were determined using a known crystal structure of FcγRIIb (Sondermann, P et al., *EMBO J.* 18:1095-1103, 1999). When a tryptophan residue critical for the binding of FcγRIIb to IgG was replaced with alanine, FcγRIIb showed remarkably reduced binding affinity to Aβ. Thus, the structure prediction was carried out by placing the N-terminal region of Aβ proximate into a tryptophan pocket of FcγRIIb.

In detail, in silico analysis was performed using the crystal structure of human FcγRIIb extracellular domain (PDB code: 2FCB, RCSB) and the NMR structure of $A\beta_{1-42}$ (PDB code: 1IYT, RCSB). Using Affinity program within InsightII (Accelrys), the N-terminal region of $A\beta_{1-42}$ was docked with the IgG binding site of FcγRIIb. The binding site was defined as an 8-Å radius from Trp92 and Trp115 residues of human FcγRIIb (hFcγRIIb). $A\beta_{1-42}$ Phe4 was first artificially located closed to Trp92 and Trp115 residues of hFcγRIIb, and the general binding procedure was then performed as follows. Molecular dynamic calculations for the binding between hFcγRIIb and Aβ were carried out using the CVFF force field. The initial structure was generated using a Monte Carlo minimization method, and simulated to generate actual non-bond contacts using a Cell Multipole method. Such simulated annealing started at 500 K, and the temperature was slowly cooled down to 300 K for stabilization through over 50 steps, followed by a final round of over 1000 steps of energy minimization for final structure calculation.

The structure calculations revealed that in a manner similar to that in which a proline residue of IgG is critical for FcγRIIb binding, the fourth residue phenylalanine of Aβ forms a strong hydrophobic bond with Trp92 and Trp115 of FcγRIIb. In contrast, the third residue glutamate of Aβ formed a relatively weak hydrophilic bond with Tyr165 of FcγRIIb. However, the fifth and sixth residues (Arg5, His6) of Aβ were not involved in FcγRIIb binding. Thus, the binding of Aβ to FcγRIIb was predicted to occur through the binding of a sequence stretch consisting of the third to seventh residues from the N-terminus of Aβ to a tryptophan pocket and Tyr165 of FcγRIIb (FIG. 9). These results indicated that Aβ signaling can be inhibited by interrupting the binding thereof to FcγRIIb.

Example 11

Interruption of the Binding Between FcγRIIb and Aβ

Based on the results of Example 10, a sequence spanning from the first to ninth residues from the N-terminus of Aβ, and a 95 to 101 sequence and a 107 to 114 sequence of mouse FcγRIIb, which are Aβ docking sites, were synthesized. Also, peptides, in which a residue involved in Aβ-cγRIIb binding in the above sequences was replaced with alanine, were synthesized. The peptides (wild type and mutant) have the sequences represented by SEQ ID Nos. 19 to 28 (panel a, FIG. 10). The synthesized peptides were individually allowed to react with a mixture of FcγRIIb-CD40 and Aβ (5 μM) or PBS. Then, luciferase activity was measured.

The NF-κB activation, induced through the binding of Aβ to FcγRIIb-CD40, was strongly inhibited by peptides #1, #4 and #9, which corresponded to binding regions in Aβ and FcγRIIb. Mutant peptides #2, #3, #6, #7 and #10, having an alanine substitution for a residue responsible for Aβ-cγRIIb binding, exhibited a sharp decrease in inhibitory effects on NF-κB activation (panel b, FIG. 10). These results indicated that the binding structure of Aβ and cγRIIb (FIG. 9), determined in Example 9, is actually important in Aβ-cγRIIb binding, and that the above peptides have the potential to inhibit Aβ signaling.

Example 12

Inhibition of Aβ-Induced Neurotoxicity Using the Peptides Inhibiting FcγRIIb-Aβ Binding Primary neuronal cells were treated with the peptides (15 μM each) prepared in Example 11 and Aβ (5 μM) for 48 hrs. Relative cell survival rates were then measured and compared with a control. Among rat primary neuronal cells, hippocampal neurons were treated with peptides #1 to #7, and rat cortical neurons were treated with peptides #8 to #10.

The binding inhibitory peptides were found to inhibit the neuronal toxicity induced by Aβ through its binding to FcγRIIb (FIG. 11). Thus, since the peptides are able to strongly inhibit the neurotoxic signaling of Aβ, they may be useful in the prevention and treatment of AD.

Example 13

Memory Test

Tg2576 mice were not used in this test because it takes a lot of time to breed the animals, and they are expensive. Instead, normal mice were used in this memory test because the same AD symptoms as in Tg2576 mice were observed when Aβ was injected into the brains of normal mice. Normal BALB/c mice were injected intracerebroventricularly (i.c.v.) with Aβ (1.855 μg/5 μl, 410 pmole) alone or in combination with a specific peptide. After one day, a Y-maze test and a passive avoidance test were performed. Memory was assessed as described in Yan et al., *Br. J. Pharmacol*, 133:89-96, 2001.

When mice received i.c.v. injection of Aβ and a peptide, peptide #1 or #9, inhibiting FcγRIIb-Aβ binding, were found to strongly reduce Aβ-induced memory decline, whereas a mutant peptide #7 failed to reverse memory decline (FIG. 12). Thus, peptides #1 and #9 may be effective in the prevention and treatment of AD.

Example 14

Evaluation of In Vivo Effects of the Binding Inhibitory Peptides

Brain specimens were prepared from the mice of Example 13 according to the same method as in Example 6. Sections were immunostained with primary antibodies, anti-Aβ antibody (Biosource, USA) plus an antibody to a marker of neurons, anti-neuron specific enolase (NSE) antibody (Axxora, Swiss) or anti-neuron specific nuclear protein (NeuN) antibody (Chemicon, USA), and with secondary antibodies, anti-mouse-FITC antibody (goat anti-mouse IgG conjugated to FITC (Santa Cruz Biotechnology, USA), anti-mouse-TRITC antibody (goat anti-mouse IgG conjugated to TRITC (Santa Cruz Biotechnology, USA), and anti-rabbit-goat-anti-mouse IgG conjugated to horseradish peroxidase (Santa Cruz Biotechnology, USA)).

Strong accumulation of intraneuronal Aβ was observed in mice treated with Aβ alone, but this phenomenon disappeared in mice treated with Aβ plus binding inhibitory peptide #1. In contrast, a strong intraneuronal Aβ staining was observed in mice treated with Aβ plus peptide #7, found not to have inhibitory capacity against Aβ-FcγRIIb binding (FIG. 13). These results indicate that the binding inhibitory peptide also effectively inhibits the binding between Aβ and FcγRIIb in vivo, and is thus useful as an effective therapeutic and preventive agent for AD.

In accordance with the present invention, as described above, an the interaction inhibitor is provided for effectively inhibiting the binding of Aβ to FcγRIIb in neuronal cells and an animal model of Alzheimer's disease, thereby reducing Aβ-induced neurotoxicity and cell death therein. Thus, the present inhibitor is useful in the diagnosis, prevention and treatment of Alzheimer's disease.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of screening for a compound that inhibits binding between amyloid β (Aβ) and Fcγ receptor IIb (FcγRIIb), comprising the steps of:
   1) adding a test compound and Aβ or an N-terminal fragment of Aβ to:
      a) FcγRIIb or an FcγRIIb extracellular domain; or
      b) a cell expressing FcγRIIb or an FcγRIIb extracellular domain,
      wherein the N-terminal fragment of Aβ binds to FcγRIIb or the FcγRIIb extracellular domain;
   2) measuring binding between FcγRIIb or the FcγRIIb extracellular domain and Aβ or the N-terminal fragment of Aβ;
   3) determining whether the test compound reduces binding between Aβ or the N-terminal fragment of Aβ and FcγRIIb or the FcγRIIb extracellular domain in comparison with a control; and
   4) selecting a test compound that inhibits binding between Aβ and FcγRIIb.

2. The method of claim 1, wherein the Aβ has the sequence represented by SEQ ID No. 29.

3. A method of screening for a compound that inhibits binding between amyloid β (Aβ) and Fcγ receptor IIb (FcγRIIb) or FcγRIIb-mediated intracellular translocation of Aβ, comprising the steps of:
   1) adding a compound to be tested and Aβ or an N-terminal fragment of Aβ to a cell expressing FcγRIIb or an FcγRIIb extracellular domain, wherein the N-terminal fragment of Aβ binds to FcγRIIb or the FcγRIIb extracellular domain;
   2) measuring a binding degree between the FcγRIIb or the FcγRIIb extracellular domain and the Aβ or the N-terminal fragment of Aβ;
   3) determining whether the compound reduces binding between the Aβ or the N-terminal fragment of Aβ and the FcγRIIb or the FcγRIIb extracellular domain in comparison with a control; and
   4) determining whether the compound inhibits FcγRIIb-mediated intracellular translocation of Aβ or the N-terminal fragment of Aβ.

4. The method of claim 3, wherein the Aβ has the sequence represented by SEQ ID No. 29.

5. The method of claim 3, wherein the N-terminal fragment of Aβ comprises amino acid residues 3 through 7 of SEQ ID NO. 29.

6. The method of claim 3, wherein Aβ is detected using a protein conjugated to a fluorescent, colorimetric or radioactive protein, compound or peptide.

7. The method of claim 3, wherein the intracellular translocation of Aβ is detected using fluorescence detection, radioactive detection or colorimetric detection apparatuses.

* * * * *

SEQUENCE LISTING

```
<160> NUMBER OF SEQ ID NOS: 32

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide primer Fc gamma
      receptor IIb-5-EcoRI

<400> SEQUENCE: 1
cgcggaattc gatggacagc aacaggact                                      29

<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide primer Fc gamma
      receptor IIb-3-KpnI

<400> SEQUENCE: 2
cgggtaccat aatgtggttc tggtagtc                                       28

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide primer Fc gamma
      receptor I-RT-5

<400> SEQUENCE: 3
ttggtgaaca cagttctcta tgtgaaaata cacaggctgc                          40

<210> SEQ ID NO 4
<211> LENGTH: 42
<212> TYPE: DNA
<213> ORGANISM: Artificial Sequence
<220> FEATURE:
```

<223> OTHER INFORMATION: Synthetic oligonucleotide primer Fc gamma
      receptor I-RT-3

<400> SEQUENCE: 4
ctatcttaca gtggctgtta cttcttcata cacgtcatcg ct                    42

<210> SEQ ID NO 5
<211> LENGTH: 40
<212> TYPE: DNA
<213> ORGANISM: Artificial Sequence
<220> FEATURE:
<223> OTHER INFORMATION: Synthetic oligonucleotide primer Fc gamma
      receptor IIa-RT-5

<400> SEQUENCE: 5
gccgatttct gcctagtgat gtgcctcctg tttgcagtgg                       40

<210> SEQ ID NO 6
<211> LENGTH: 40
<212> TYPE: DNA
<213> ORGANISM: Artificial Sequence
<220> FEATURE:
<223> OTHER INFORMATION: Synthetic oligonucleotide primer Fc gamma
      receptor IIa-RT-3

<400> SEQUENCE: 6
tcatttgtcc tgtggagcct ctttccgact gacagggatc                       40

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide primer for beta
      actin-5 for RT-PCR

<400> SEQUENCE: 7
gcgtccaccc gcgag                                                  15

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide primer for beta
      actin-3 for RT-PCR

<400> SEQUENCE: 8
tatagcaggg tcaac                                                  15

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide primer Fc gamma
      receptor IIb[I232T]-5

<400> SEQUENCE: 9
gctgtcgctg gaactgtagc tgcc                                        24

<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucleotide primer Fc gamma
      receptor IIb[I232T]-3

-continued

<400> SEQUENCE: 10
ggcagctaca gcagttccag cgacagc                                            27

<210> SEQ ID NO 11
<211> LENGTH: 64
<212> TYPE: DNA
<213> ORGANISM: Artificial Sequence
<220> FEATURE:
<223> OTHER INFORMATION: Synthetic RNA oligonucleotide siFc gamma
      receptor IIb-5

<400> SEQUENCE: 11
gatcccctcg gagagccact tatgctttca agagaagcat aagtggctct ccgattttg       60 gaaa                                                                    64

<210> SEQ ID NO 12
<211> LENGTH: 71
<212> TYPE: DNA
<213> ORGANISM: Artificial Sequence
<220> FEATURE:
<223> OTHER INFORMATION: Synthetic RNA oligonucleotide siFc gamma
      receptor IIb-3

<400> SEQUENCE: 12
agcttttcca aaaatcggag agccacttat gcttctcttg aaagcataag tggctctccc      60
gaggagtcgg g                                                           71

<210> SEQ ID NO 13
<211> LENGTH: 64
<212> TYPE: DNA
<213> ORGANISM: Artificial Sequence
<220> FEATURE:
<223> OTHER INFORMATION: Synthetic RNA oligonucleotide siRAGE-5 sense
      oligomer

<400> SEQUENCE: 13
gatccccgct ccggatgaag aatcagttca agagactgat tcttcatccg gagcttttg      60 gaaa                                                                    64

<210> SEQ ID NO 14
<211> LENGTH: 70
<212> TYPE: DNA
<213> ORGANISM: Artificial Sequence
<220> FEATURE:
<223> OTHER INFORMATION: Synthetic RNA oligonucleotide siRAGE-3
      antisense oligomer

<400> SEQUENCE: 14
agcttttcca aaaagctccg gatgaagaat cagtctcttg aactgattct tcatccggag     60
cggagtcggg                                                             70

<210> SEQ ID NO 15
<211> LENGTH: 27
<212> TYPE: DNA
<213> ORGANISM: Artificial Sequence
<220> FEATURE:
<223> OTHER INFORMATION: Synthetic oligonucleotide primer Fc gamma
      receptor IIb-ED-5-NheI

<400> SEQUENCE: 15
gctagcgcta tggacagcaa caggact                                           27

<210> SEQ ID NO 16

```
<211> LENGTH: 30
<212> TYPE: DNA
<213> ORGANISM: Artificial Sequence
<220> FEATURE:
<223> OTHER INFORMATION: Synthetic oligonucleotide primer Fc gamma
      receptor
      IIb-ED-3-HindIII

<400> SEQUENCE: 16
aagcttggga ggcaacgaac tgctggattt                                        30

<210> SEQ ID NO 17
<211> LENGTH: 33
<212> TYPE: DNA
<213> ORGANISM: Artificial Sequence
<220> FEATURE:
<223> OTHER INFORMATION: Synthetic oligonucleotide primer CD40-TM+cyto-
      5-HindIII

<400> SEQUENCE: 17
cccaagcttg gggccctggt ggtgatcccc atc                                    33

<210> SEQ ID NO 18
<211> LENGTH: 28
<212> TYPE: DNA
<213> ORGANISM: Artificial Sequence
<220> FEATURE:
<223> OTHER INFORMATION: Synthetic oligonucleotide primer CD40-TM+cyto-
      3-KpnI

<400> SEQUENCE: 18
cgggtaccat tcactgtctc tcctgcac                                          28

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide #1 for interaction inhibitor

<400> SEQUENCE: 19

Asp Ala Glu Phe Arg His Asp Ser Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide #2 for interaction inhibitor

<400> SEQUENCE: 20

Asp Ala Ala Phe Arg His Asp Ser Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide #3 for interaction inhibitor

<400> SEQUENCE: 21

Asp Ala Glu Ala Arg His Asp Ser Gly
1               5

<210> SEQ ID NO 22
<211> LENGTH: 9
```

```
<212> TYPE: PRT
<213> ORGANISM: Artificial Sequence
<220> FEATURE:
<223> OTHER INFORMATION: Synthetic peptide #4 for interaction inhibitor

<400> SEQUENCE: 22

Asp Ala Glu Phe Ala His Asp Ser Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide #5 for interaction inhibitor

<400> SEQUENCE: 23

Asp Ala Glu Phe Arg Ala Asp Ser Gly
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide #6 for interaction inhibitor

<400> SEQUENCE: 24

Asp Ala Glu Phe Arg His Ala Ser Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide #7 for interaction inhibitor

<400> SEQUENCE: 25

Asp Ala Glu Ala Arg His Ala Ser Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide #8 for interaction inhibitor

<400> SEQUENCE: 26

Gln Leu Val Phe Leu Glu Gly
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide #9 for interaction inhibitor

<400> SEQUENCE: 27

Arg Cys His Ser Trp Arg Asn Lys
1               5

<210> SEQ ID NO 28
<211> LENGTH: 8
<212> TYPE: PRT
<213> ORGANISM: Artificial Sequence
```

```
<220> FEATURE:
<223> OTHER INFORMATION: Synthetic peptide #10 for interaction inhibitor

<400> SEQUENCE: 28

Arg Cys His Ser Ala Arg Asn Lys
1               5

<210> SEQ ID NO 29
<211> LENGTH: 43
<212> TYPE: PRT
<213> ORGANISM: Artificial Sequence
<220> FEATURE:
<223> OTHER INFORMATION: Amyloid beta peptide

<400> SEQUENCE: 29

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

<210> SEQ ID NO 30
<211> LENGTH: 1633
<212> TYPE: DNA
<213> ORGANISM: Artificial Sequence
<220> FEATURE:
<223> OTHER INFORMATION: human Fc gamma receptor IIb DNA sequence

<400> SEQUENCE: 30
agaatttgtt tgccctctag ggtagaatcc gccaagcttt gagagaaggc tgtgactgct      60
gtgctctggg cgccagctcg ctccagggag tgatgggaat cctgtcattc ttacctgtcc     120
ttgccactga gagtgactgg gctgactgca agtcccccca gccttggggt catatgcttc     180
tgtggacagc tgtgctattc ctggctcctg ttgctgggac acctgcagct cccccaaagg     240
ctgtgctgaa actcgagccc cagtggatca acgtgctcca ggaggactct gtgactctga     300
catgccgggg gactcacagc cctgagagcg actccattca gtggttccac aatgggaatc     360
tcattcccac ccacacgcag cccagctaca ggttcaaggc caacaacaat gacagcgggg     420
agtacacgtg ccagactggc cagaccagcc tcagcgaccc tgtgcatctg actgtgcttt     480
ctgagtggct ggtgctccag acccctcacc tggagttcca ggagggagaa accatcgtgc     540
tgaggtgcca cagctggaag gacaagcctc tggtcaaggt cacattcttc cagaatggaa     600
aatccaagaa atttttcccgt tcggatccca acttctccat cccacaagca aaccacagtc     660
acagtggtga ttaccactgc acaggaaaca taggctacac gctgtactca tccaagcctg     720
tgaccatcac tgtccaagct cccagctctt caccgatggg gatcattgtg gctgtggtca     780
ctgggattgc tgtagcggcc attgttgctg ctgtagtggc cttgatctac tgcaggaaaa     840 agcggattte agctctccca ggataccctg agtgcaggga aatgggagag accctccctg     900
agaaaccagc caatcccact aatcctgatg aggctgacaa agttggggct gagaacacaa     960
tcacctattc acttctcatg caccccggatg ctctggaaga gctgatgac cagaaccgta    1020 tttagtctcc attgtcttgc attgggattt gagaagaaaa tcagagaggg aagatctggt    1080
atttcctggc ctaaattccc cttggggagg acagggagag gctgcagttc aaaagagaa    1140 ggtttcttcc agagtcatct acctgagtcc tgaagctccc tgtcctgaaa gccacagaca    1200
atatggtccc aaatgaccga ctgcaccttc tgtgcttcag ctcttcttga catcaaggct    1260
cttccgttcc acatccacac agccaatcca attaatcaaa ccactgttat taacagataa    1320
```

```
tagcaacttg ggaaatgctt atgttacagg ttacgtgaga acaatcatgt aaatctatat    1380
gatttcagaa atgttaaaat agactaacct ctaccagcac attaaaagtg attgtttctg    1440
ggtgataaaa ttattgatga tttttatttt ctttattttt ctataaagat catatattac    1500
ttttataata aaacattata aaaacaacat tctgtttacc ttttcaaggc tgtattggtt    1560
ggagtgtaga ctgaactgcc tggggtctgt ttctcttcag tgatgagact cttaggaagg    1620
caggaatgga tag                                                        1633
```

<210> SEQ ID NO 31
<211> LENGTH: 310
<212> TYPE: PRT
<213> ORGANISM: Artificial Sequence
<220> FEATURE:
<223> OTHER INFORMATION: human Fc gamma receptor IIb amino acid sequence

<400> SEQUENCE: 31

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
    290                 295                 300
```

Asp Asp Gln Asn Arg Ile
305                 310

<210> SEQ ID NO 32
<211> LENGTH: 310
<212> TYPE: PRT
<213> ORGANISM: Artificial Sequence
<220> FEATURE:
<223> OTHER INFORMATION: human Fc gamma receptor IIb[I232T] mutant amino
      acid sequence

<400> SEQUENCE: 32

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
                20                  25                  30

Ala Val Leu Phe Leu Ala Pro Val Ala Gly Thr Pro Ala Ala Pro Pro
            35                  40                  45

Lys Ala Val Leu Lys Leu Glu Pro Gln Trp Ile Asn Val Leu Gln Glu
        50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
210                 215                 220

Ile Val Ala Val Val Thr Gly Thr Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
290                 295                 300

Asp Asp Gln Asn Arg Ile
305                 310